United States Patent
Jeong et al.

(10) Patent No.: US 11,027,029 B2
(45) Date of Patent: Jun. 8, 2021

(54) PEPTIDE THIOUREA DERIVATIVE, RADIOISOTOPE LABELED COMPOUND CONTAINING SAME, AND PHARMACEUTICAL COMPOSITION CONTAINING SAME AS ACTIVE INGREDIENT FOR TREATING OR DIAGNOSING PROSTATE CANCER

(71) Applicant: CELLBION CO., LTD, Seoul (KR)

(72) Inventors: Jae Min Jeong, Seoul (KR); Sung-Hyun Moon, Seoul (KR); Yun-Sang Lee, Seoul (KR)

(73) Assignee: Cellbion Co., Ltd, Seoul (KR)

( * ) Notice: Subject to any disclaimer, the term of this patent is extended or adjusted under 35 U.S.C. 154(b) by 0 days.

(21) Appl. No.: 15/774,632

(22) PCT Filed: Nov. 9, 2016

(86) PCT No.: PCT/KR2016/012849
§ 371 (c)(1),
(2) Date: May 9, 2018

(87) PCT Pub. No.: WO2017/082620
PCT Pub. Date: May 18, 2017

(65) Prior Publication Data
US 2018/0339071 A1 Nov. 29, 2018

(30) Foreign Application Priority Data
Nov. 9, 2015 (KR) .................. 10-2015-0156536

(51) Int. Cl.
*A61K 51/04* (2006.01)
*C07D 257/02* (2006.01)
*A61P 35/00* (2006.01)
*G01N 33/60* (2006.01)
*A61K 31/41* (2006.01)
*G01N 33/574* (2006.01)
*C07D 255/02* (2006.01)
*C07F 5/00* (2006.01)

(52) U.S. Cl.
CPC ............ *A61K 51/044* (2013.01); *A61K 31/41* (2013.01); *A61K 51/0402* (2013.01); *A61K 51/0482* (2013.01); *A61K 51/0497* (2013.01); *A61P 35/00* (2018.01); *C07D 255/02* (2013.01); *C07D 257/02* (2013.01); *C07F 5/003* (2013.01); *G01N 33/574* (2013.01); *G01N 33/60* (2013.01)

(58) Field of Classification Search
CPC combination set(s) only.
See application file for complete search history.

(56) References Cited

U.S. PATENT DOCUMENTS

| 8,926,944 | B2 | 1/2015 | Babich et al. | ............... 424/1.65 |
| 2010/0178246 | A1* | 7/2010 | Babich | .................. A61K 31/18 |
| | | | | 424/1.65 |
| 2012/0269726 | A1 | 10/2012 | Babich et al. | ............... 424/1.85 |

FOREIGN PATENT DOCUMENTS

| JP | 2015-089881 A | 5/2015 |
| KR | 10-2004-044562 A | 5/2004 |
| KR | 10-2012-0048250 A | 5/2012 |
| KR | 10-2015-0104092 A | 9/2015 |
| WO | WO 2010/014933 A2 | 2/2010 |

OTHER PUBLICATIONS

Däpp et al. "PEGylation, increasing Specific Activity and Multiple Dosing as Strategies to Improve the Risk-Benefit Profile of Targeted Radionuclide Therapy with $^{177}$Lu-DOTA-Bombesin Analogues" EJNMMI Research 2012 2:24.
Eder et al. "$^{68}$Ga-Complex Lipophilicity and the Targeting Property of a Urea-Based PSMA Inhibitor for PET Imaging" Bioconjugate Chemistry 2012 23:688-697.

* cited by examiner

*Primary Examiner* — Michael G. Hartley
*Assistant Examiner* — Leah H Schlientz
(74) *Attorney, Agent, or Firm* — Licata & Tyrrell P.C.

(57) ABSTRACT

The present invention relates to a peptide thiourea derivative, a pharmaceutically acceptable salt thereof, a radioisotope labeled compound comprising the same, and a pharmaceutical composition for treating or diagnosing prostate cancer comprising the same as an active ingredient. The peptide thiourea derivative of the present invention is excellent in stability in human serum when it is administered in vivo and not only binds well to PSMA expressed in prostate cancer but also inhibits excellently PSMA at a low concentration. Besides, the derivative of the invention has a high water-solubility and can be excreted through the kidney not through the bile passage so that a clear image of the tumor region of prostate cancer can be obtained. Therefore, the derivative of the present invention can be effectively used as a pharmaceutical composition for treating and diagnosing prostate cancer.

12 Claims, 4 Drawing Sheets

[Figure 1a]
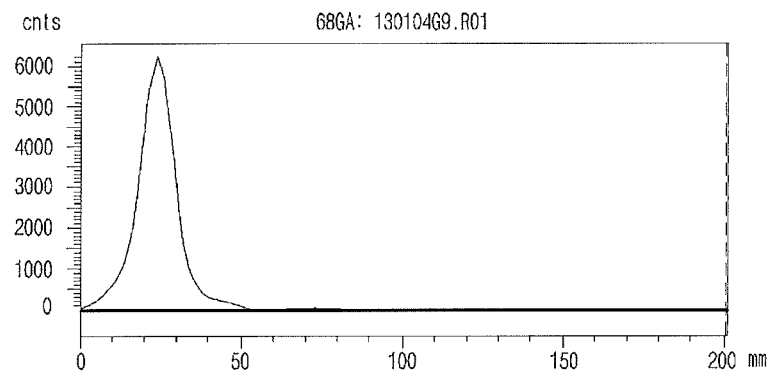
[Figure 1b]
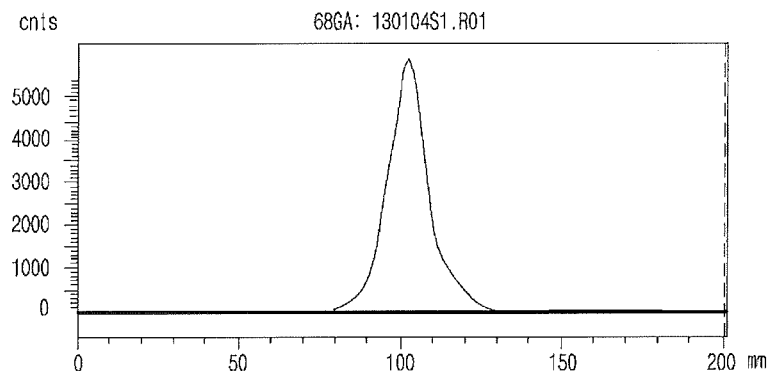
[Figure 1c]
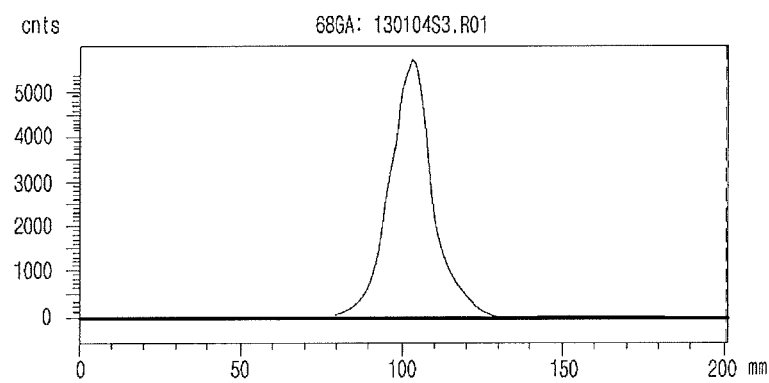

[Figure 2a]
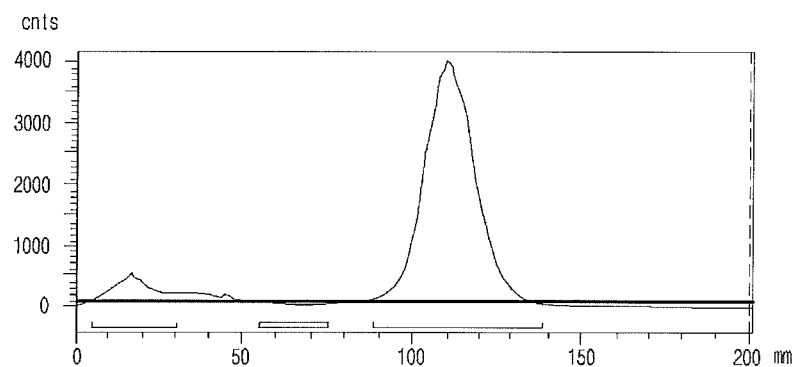
[Figure 2b]
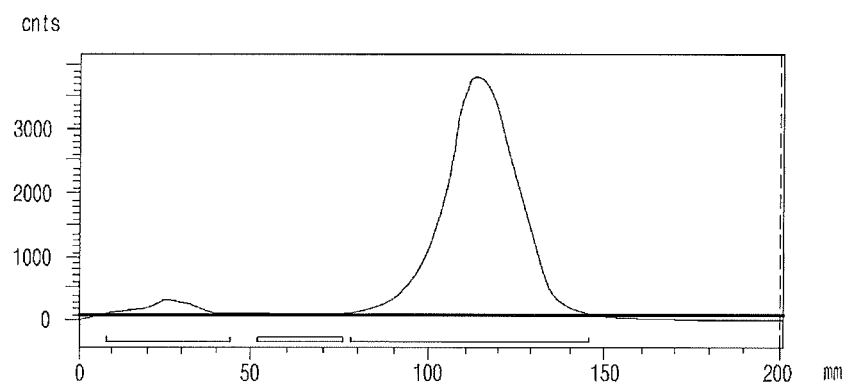
[Figure 2c]
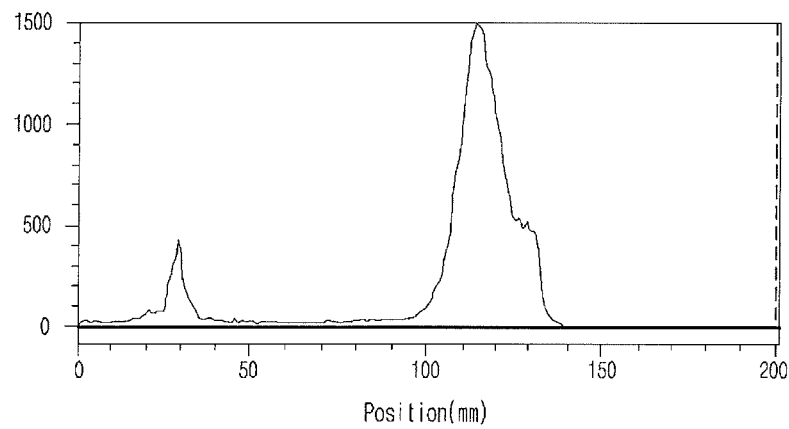

[Figure 3a]
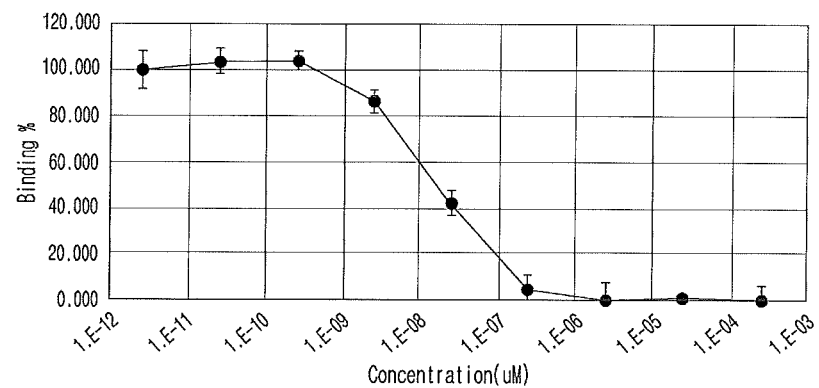
[Figure 3b]
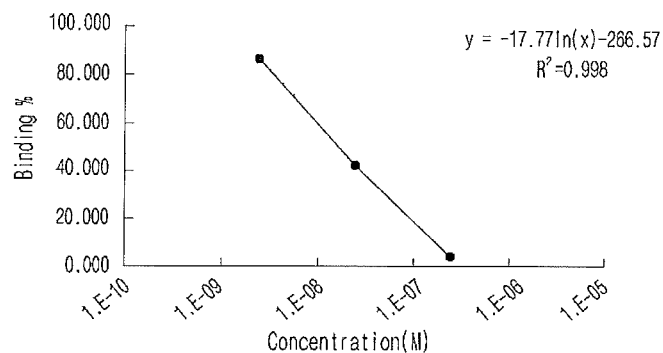

[Figure 4a]
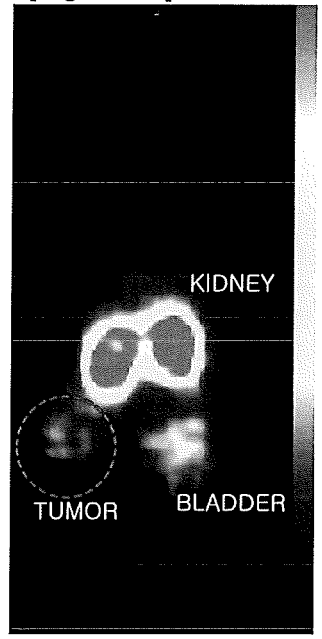
[Figure 4b]
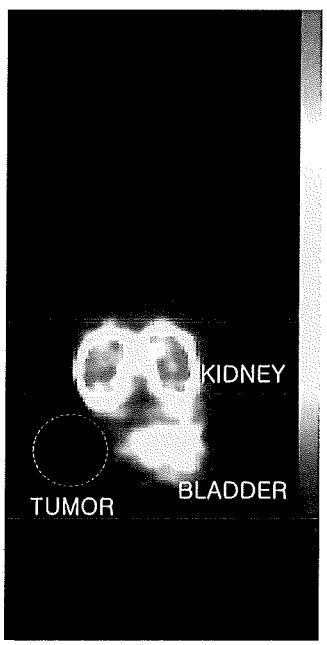

US 11,027,029 B2

PEPTIDE THIOUREA DERIVATIVE, RADIOISOTOPE LABELED COMPOUND CONTAINING SAME, AND PHARMACEUTICAL COMPOSITION CONTAINING SAME AS ACTIVE INGREDIENT FOR TREATING OR DIAGNOSING PROSTATE CANCER

This patent application is the National Stage of International Application No. PCT/KR2016/012849 filed Nov. 9, 2016, which claims the benefit of priority from Korean Application No. 10-2015-0156536, filed Nov. 9, 2015, each of which are herein incorporated by reference in their entirety.

BACKGROUND OF THE INVENTION

1. Field of the Invention

The present invention relates to a peptide thiourea derivative, a radioisotope labeled compound comprising the same, and a pharmaceutical composition for treating or diagnosing prostate cancer comprising the same as an active ingredient.

2. Description of the Related Art

Prostate cancer is one of the most common urogenital tumors worldwide. In USA, about 380,000 people were diagnosed with prostate cancer in 1997, among which 41,800 people died, indicating that the death rate of this disease was the second highest next to lung cancer. In Korea, prostate cancer is rapidly increasing due to aging and westernization of diet. Therefore, early imaging diagnosis and treatment of prostate cancer has become a big issue not only in Korea but also in the whole world.

Prostate cancer begins to grow in the tissues around the prostate gland and as it grows it migrates to other important organs such as the lung and the bone. In the early stage, there are few symptoms but as prostate cancer grows it causes problems such as urethral compression and urinary tract obstruction and further it migrates to the spine or pelvis bone with serious complications.

For the diagnosis of prostate cancer, imaging diagnostic methods such as SPECT (Single Photon Emission Computed Tomography) and PET (Positron Emission Tomography) have been used, wherein the biochemical changes occurring in tumor cells are expressed in tomographic images and three-dimensional images by using radioisotope labeled substances emitting gamma rays or positrons to indicate the presence of cancer or the distribution thereof.

These imaging diagnostic methods have recently been propagated because of the improvement of image quality with the development of CT combined SPECT-CT/MRI and PET-CT/MRI.

The radiopharmaceuticals used as an imaging agent for prostate cancer use the ligand binding to the protein (Prostate Specific Membrane Antigen: PSMA) expressed specifically in prostate cancer. The most representative ligand binding to PSMA is a peptide derivative such as Glu-urea-Lys (GUL) or Glu-urea-Cys (GUC). So, the radiopharmaceuticals prepared by labeling a radio-isotope to such a peptide ligand can be used for specifically imaging prostate cancer expressing PSMA with PET or SPECT or for treating prostate cancer (M Eder, et. el., Bioconjugate Chem 2012, 23:688-697).

The radio-isotopes used for labeling peptides are mainly alpha-ray emitting radionuclides, beta-ray emitting radionuclides, gamma-ray emitting radionuclides, and positron-beam emitting radionuclides. Among them, alpha-ray emitting radionuclides and beta-ray emitting radionuclides are used for the treatment and gamma-ray emitting radionuclides and positron-beam emitting radionuclides are used for the diagnosis by nucleus imaging.

The method for labeling ligands with radio-isotopes is exemplified by the method to bind radio-isotopes directly to ligands or the method to combine bifunctional chelating agents (BFCA) such as DTPA, DOTA, TETA, HYNIC, N2S2, and MAG3 to peptide before labeling the peptide with radio-isotopes by chelation. The direct binding method is mainly used to bind I-125, which can not bind various radio-isotopes. In the meantime, the method using a bifunctional chelating agent (BFCA) can label various radio-isotopes. The kind of the bifunctional chelating agent (BFCA) is properly selected according to the ligand, and the solubility thereof has been improved.

TABLE 1

Bifunctional chelating agents (BFCA) used depending on the type of ligand peptide

| Group | Peptide | BFCA | Targeted disease |
|---|---|---|---|
| Somatostatin (SST) analogues | octreotide | DTPATETAHYNIC | tumor (neuroendocrine) |
| Somatostatin (SST) analogues | Tyr³-octreotide (Y3-TETA) | TETAHYNIC | tumor (neuroendocrine) |
| Somatostatin (SST) analogues | vapreotide (RC-160) | S—S (direct)HYNIC | tumor (neuroendocrine) |
| BN/GRP analogues | BN | N2S2HYNIC | tumor |
| VIP analogues | VIP | MAG3 | tumor |
| RGD-containing peptides/RGD-peptidomimetics | | HYNIC | thrombosis |
| R-MSH analogues | CCMSH | S—S (direct) | tumor (breast, prostate) |
| SP analogues | SP | DTPA | tumor |
| chemotactic peptides | fMLF | HYNIC | infection/inflammation |

As for the technique relating to the radiopharmaceuticals for prostate cancer imaging, US 2012/0269726 A1 describes a compound comprising a GUL derivative and a pyridine structure for labeling the radio-isotope such as Tc-99m or Re-188. However, in this description, such a bifunctional chelating agent as NOTA or DOTA is not included, so isotopes such as Ga-68 cannot be labeled.

WO 2010/014933 A2 describes a GUL derivative labeled with F-18 or I-125 after the introduction of halogen in phenyl-ring by thiourea binding. However, in this description, such a bifunctional chelating agent as NOTA or DOTA is not included, either, so metal isotopes such as Ga-68 cannot be labeled.

The compounds labeled with isotopes such as iodine or F-18 described above are lipophilic radiopharmaceuticals. These lipophilic pharmaceuticals are mainly excreted through the small and large intestines via bile passage, so that they stay in the body for a long time. Therefore, the image showing the inside abdominal cavity is very complicated, indicating it is difficult to obtain a clean image of a desired region. In the meantime, the water-soluble medicines are excreted through the kidney, indicating that they are gathered only in the kidney and bladder and excreted fast, after which radioactivity is hardly left. Therefore, a clean image of a desired region can be obtained.

The water-soluble radiopharmaceuticals for imaging developed so far are peptide ligands combined with bifunctional chelating agents. The linker connecting the peptide with the bifunctional chelating agent has an amide bond. However, the amide bond of the linker can be hydrolyzed by peptidase or lysosomal enzyme in vivo depending on the type of the ligand. Once the linker is broken by hydrolysis, the bifunctional chelating agent and the peptide ligand labeled with a radio-isotope are separated from each other, indicating that the radio-isotope cannot go to the prostate cancer region, resulting in the difficulty in treatment or diagnosis of prostate cancer (Simone Dapp, et al. EJNMMI Res. 2012 Jun. 9; 2(1):24).

The present inventors tried to develop radioactive pharmaceuticals with increased stability not to be easily hydrolyzed in vivo and specific binding activity to prostate cancer. As a result, the present inventors confirmed that the derivative prepared by conjugating a bifunctional chelating agent with a prostate specific peptide ligand through a linker which is not hydrolyzed by a protease in serum was excellent in stability in human serum when it is administered in vivo; was binding excellently to PSMA expressed competitively in prostate cancer; and was excellent in suppressing PSMA at a low concentration. The compound labeled with the radio-isotope above also exhibited the same effect as the above and showed high water-solubility, so that it can be excreted into the kidney rather than the bile passage, indicating that a clear image of the prostate cancer region can be obtained. Therefore, the present inventors confirmed that the derivative of the invention can be effectively used as a pharmaceutical composition for treating or diagnosing prostate cancer, leading to the completion of the present invention.

SUMMARY OF THE INVENTION

It is an object of the present invention to provide a peptide thiourea derivative or a pharmaceutically acceptable salt of the same.

It is another object of the present invention to provide a preparation method of the peptide thiourea derivative above.

It is further an object of the present invention to provide a labeled compound prepared by coordinating a metallic radio-isotope to the peptide thiourea derivative or the pharmaceutically acceptable salt thereof.

It is also an object of the present invention to provide a pharmaceutical composition for treating or diagnosing prostate cancer comprising the labeled compound above as an active ingredient.

It is also an object of the present invention to provide a radiopharmaceutical for imaging prostate cancer comprising the peptide thiourea derivative or the pharmaceutically acceptable salt thereof as an active ingredient.

It is also an object of the present invention to provide a kit for treating or diagnosing prostate cancer comprising the peptide thiourea derivative or the pharmaceutically acceptable salt thereof as an active ingredient.

To achieve the above objects, the present invention provides the compound represented by formula below or the pharmaceutically acceptable salt thereof.

[Formula 1]

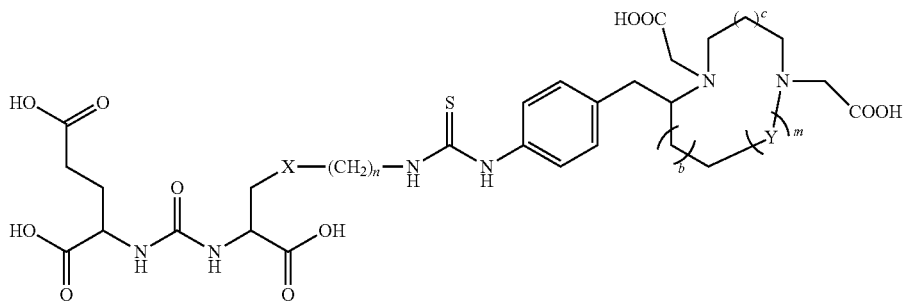

(In formula 1,
X is single bond, —O— or —S—;
n is an integer of 1~5;
Y is —N(CH$_2$COOH)(CH$_2$)$_a$CH$_2$CH$_2$—,
m is an integer of 1 or 2; and
a, b and c are independently an integer of 0 or 1).

The present invention also provides a preparation method of the compound represented by formula 1 comprising the step of preparing the compound represented by formula 1 by reacting the compound represented by formula 2 and the compound represented by formula 3 (step 1), as shown in reaction formula 1 below.

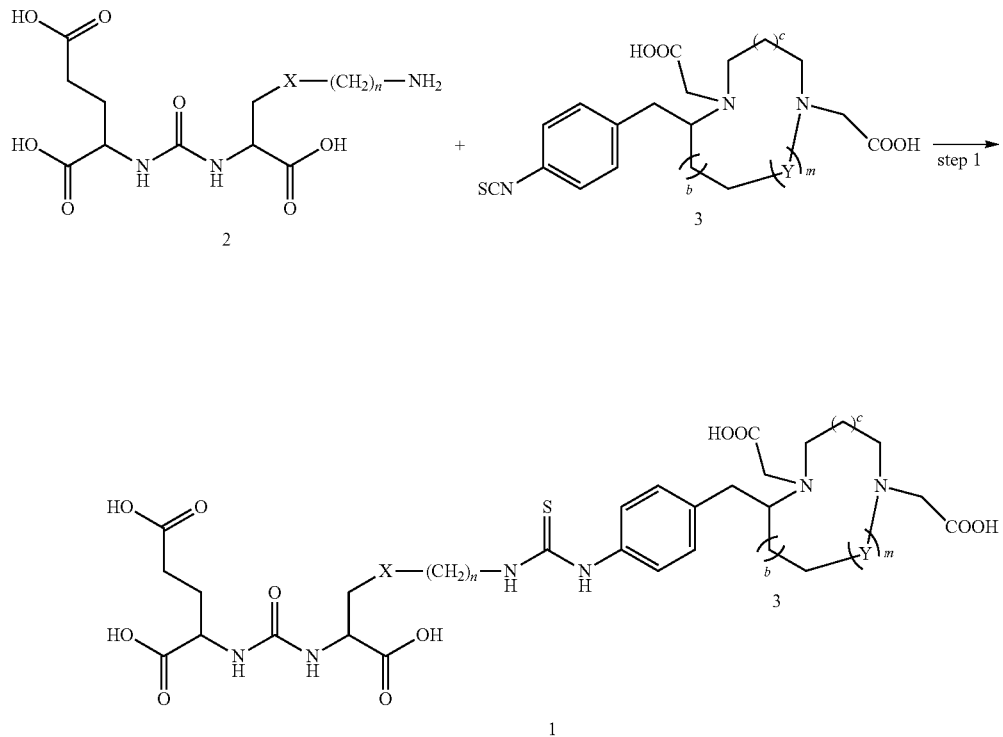

[Reaction Formula 1]

(In reaction formula 1,
X, n, Y, m, a, b, and c are as defined in formula 1).

Further, the present invention provides a labeled compound prepared by coordinating a metallic radio-isotope to the peptide thiourea derivative or the pharmaceutically acceptable salt thereof.

The present invention also provides a pharmaceutical composition for treating or diagnosing prostate cancer comprising the labeled compound above as an active ingredient.

The present invention also provides a radiopharmaceutical for imaging prostate cancer comprising the compound represented by formula 1 or the pharmaceutically acceptable salt thereof as an active ingredient.

In addition, the present invention provides a kit for treating or diagnosing prostate cancer comprising the compound represented by formula 1 or the pharmaceutically acceptable salt thereof as an active ingredient.

Advantageous Effect

The peptide thiourea derivative of the present invention is excellent in stability in human serum when it is administered in vivo and is not only excellent in binding to PSMA expressed competitively in prostate cancer but also excellent in suppressing PSMA at a low concentration; and the derivative is excreted into the kidney rather than the bile passage because of its high water-solubility so that it is accumulated in prostate cancer tissues and emits radiation to the prostate cancer region, indicating that the derivative can be effectively used as a pharmaceutical composition for treating and diagnosing prostate cancer.

BRIEF DESCRIPTION OF THE DRAWINGS

The application of the preferred embodiments of the present invention is best understood with reference to the accompanying drawings, wherein:

FIGS. 1a-1c are graphs illustrating the TLC (moving phase: 0.1 M $Na_2CO_3$, stationary phase: ITLC) results of Ga-68-NOTA-GUL according to the present invention, wherein FIG. 1a shows non-labeled Ga-68, FIG. 1b shows Ga-68-NOTA-GUL, and FIG. 1c displays Ga-68-NOTA-GUL cultured with human serum for 2 hours.

FIGS. 2a-2c are graphs illustrating the TLC (moving phase: 0.1 M $Na_2CO_3$, stationary phase: ITLC) results of Ga-68-DOTA-GUL according to the present invention, wherein FIG. 2a shows non-labeled Ga-68, FIG. 2b shows Ga-68-DOTA-GUL, and FIG. 2c displays Ga-68-DOTA-GUL cultured with human serum for 2 hours.

FIG. 3a is a graph illustrating the inhibition rate of the binding between PSMA positive 22Rv1 cells and I-125-MIP-1072 according to the concentration of the Ga-NOTA-SCN-GUL of the present invention, and FIG. 3b is a graph illustrating the $IC_{50}$ of Ga-NOTA-SCN-GUL analyzed by nonlinear regression analysis (y=−17.77 ln(x)−266.57, R2=0.998), $IC_{50}$=18.3 nM).

FIGS. 4a-4b are the PET images obtained one hour after the intravenous injection of the Ga-68-NOTA-SCN-GUL of the invention GUL in the mouse transplanted with 22Rv1 cells. In FIG. 4a, 22Rv1 cancer is shown in the left bottom but in FIG. 4b, Ga-68-NOTA-SCN-GUL is not observed in the cancer region after the injection of MIP-1072.

BEST MODE

Hereinafter, examples and experimental examples of the present invention will be specifically described and exemplified. However, the present invention is not limited by the following examples and experimental examples.

Example 1: Preparation of (S)-2-(3-((S)-1-carboxy-5-(3-(4-((1,4,7-tris(carboxymethyl)-1,4,7-triazonane-2-yl)methyl)phenyl)thioureido)pentyl)ureido)pentanedioic acid (GUL-SCN-NOTA)

Step 1: Preparation of (S)-di-tert-butyl 2-(1H-imidazole-1-carboxamido)pentanedioate

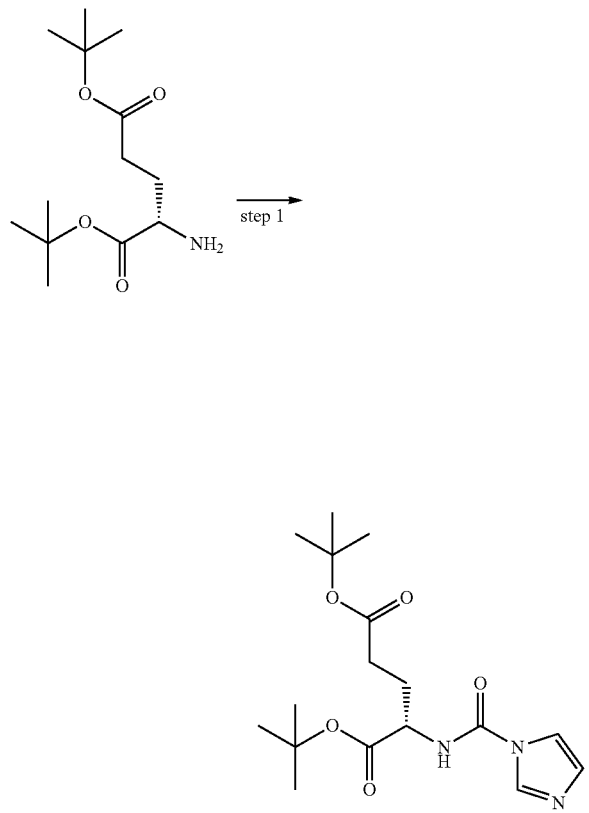

L-di-tert-butyl glutamate hydrochloride (1.50 g, 5.1 mmol) was dissolved in dichloromethane (15 mL) and then cooled to 0° C., to which triethylamine (1.74 mL, 12.5 mmol) and 4-(dimethylamino)pyridine were added. The mixture was stirred for 5 minutes, then 1,1'-carbonyldiimidazole (981 mg, 6.05 mmol) was added thereto. The temperature of the mixture was raised to room temperature, followed by stirring for 18 hours. 30 mL of dichloromethane was added thereto for the dilution. The mixture was washed with saturated sodium bicarbonate solution (10 mL), water (2×10 mL), and brine (10 mL). Then, the organic layer was dehydrated with sodium sulfate. The mixture was filtered and the filtrate was dried under reduced pressure, followed by the treatment of hexane/ethylacetate solution. As a result, a white solid material was obtained. The obtained white solid material was washed with hexane (50 mL) and the final white solid material was analyzed by instrumental analysis.

Yield: 1.44 g, 80%;

$^1$H-NMR (DMSO-$d_6$, 600 MHz) δ 8.29 (s, 1H), 7.73 (s, 1H), 7.05 (s, 1H), 7.01 (s, 1H), 4.24 (m, 1H), 2.36 (t, J=7.26 Hz, 2H), 2.03 (m, 1H), 1.87 (m, 1H), 1.42 (s, 9H), 1.39 (s, 9H).

Mass spectrum (ESI$^+$), m/z=354 [M+H]$^+$.

Step 2: Preparation of (9S,13S)-tri-tert-butyl 3,11-dioxo-1-phenyl-2-oxa-4,10,12-triazapentadekan-9,13,15-tricarboxylate

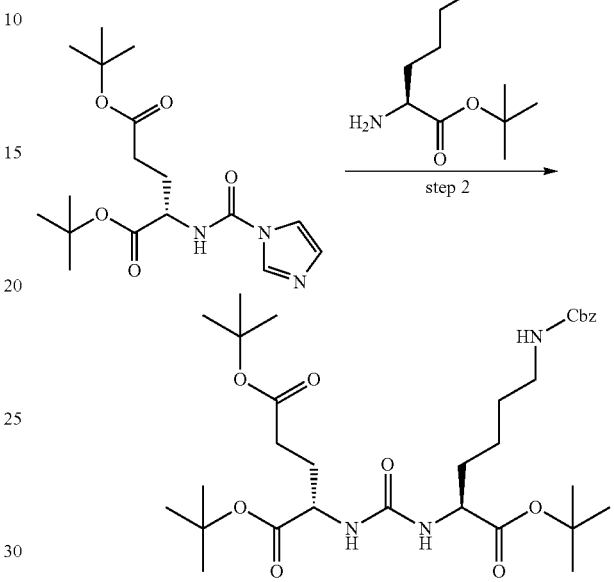

(S)-di-tert-butyl 2-(1H-imidazole-1-carboxamido)pentanedioate (780 mg, 2.208 mmol) prepared in step 1 was dissolved in dichloromethane (7.8 mL), and then cooled to 0° C., to which triethylamine (0.615 mL, 4.417 mmol) and methyl trifluoromethanesulfonate (MeOTf) (0.252 mL, 2.230 mmol) were added. The temperature of the mixture was raised to room temperature while stirring, followed by further stirring for 30 minutes at room temperature. The reaction mixture was added with (S)-tert-butyl 2-amino-6-(((benzyloxy)carbonyl)amino)hexanoate (743 mg, 2.208 mmol) and heated at 40° C., followed by stirring overnight. Upon completion of the reaction, the solution was dried under reduced pressure. Then, a solid product was obtained by using ether and hexane.

Yield: 1.18 g, 86%;

Mass spectrum (ESI$^+$), m/z=622 [M+H]$^+$.

Step 3: Preparation of (S)-di-tert-butyl 2-(3-((S)-6-amino-1-tert-butoxy-1-oxohexane-2-yl)ureido)pentanedioate

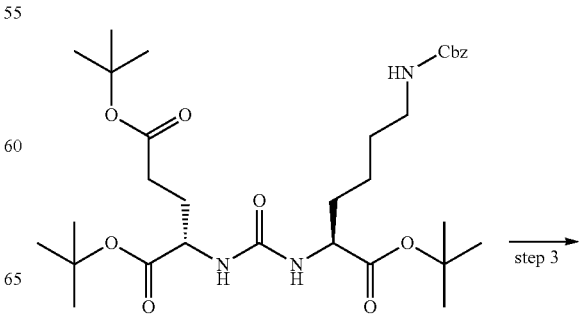

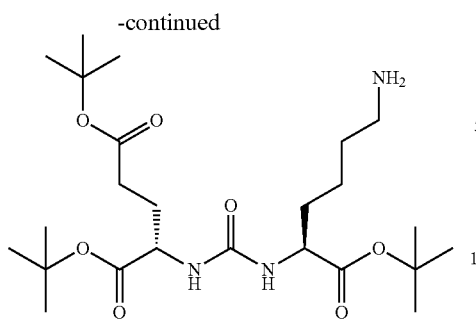

Ammonium formate (314 mg, 4.986 mmol) and 10 wt % palladium carbon (100 mg) were added to the (9S,13S)-tri-tert-butyl 3,11-dioxo-1-phenyl-2-oxa-4,10,12-triazapentadekan-9,13,15-tricarboxylate (310 mg, 0.499 mmol) ethanol (5 mL) solution prepared in step 2, followed by stirring at room temperature for 4 hours. Upon completion of the reaction, the mixture was filtered by using Celite 545 and then washed with ethylacetate (25 mL×3). A white solid product was obtained by distillating the filtrate under reduced pressure.

Yield: 243 mg, 98%.

$^1$H-NMR (DMSO-$d_6$, 600 MHz) δ 8.43 (s, 1H), 8.10-7.10 (br, 1H), 6.50 (m, 2H), 4.01 (m, 1H), 3.92 (m, 1H), 2.69 (m, 2H), 2.17 (m, 2H), 1.83 (m, 1H), 1.70-1.49 (m, 4H), 1.38 (m, 27H), 1.29 (m, 2H).

Mass spectrum (ESI$^+$), m/z=488 [M+H]$^+$.

Step 4: Preparation of 2,2',2"-(2-(4-(3-((S)-6-(tert-butoxy)-5-(3-((S)-1,5-di-tert-butoxy-1,5-dioxopentane-2-yl)ureido)-6-oxohexyl)thioureido)benzyl)-1,4,7-triazonane-1,4,7-trityl)triacetic acid

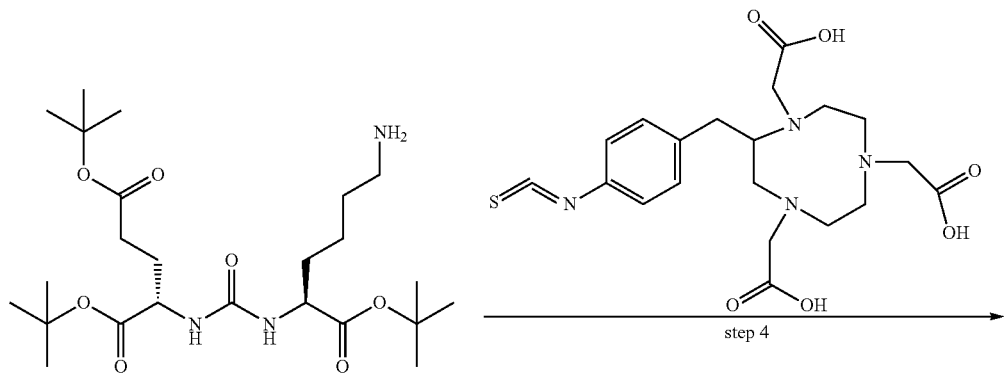

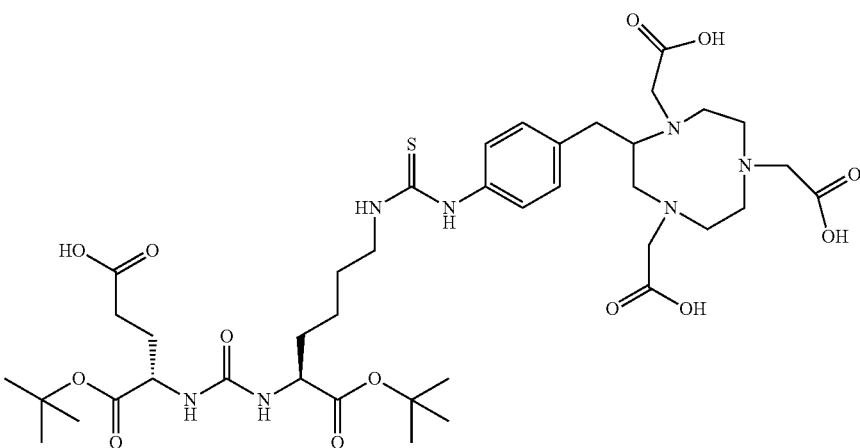

(S)-di-tert-butyl 2-(3-((S)-6-amino-1-tert-butoxy-1-oxo-hexane-2-yl)ureido)pentanedioate (47.8 mg, 0.0982 mmol), 2,2',2''-(2-(4-isothiocyanatobenzyl)-1,4,7-triazonane-1,4,7-triyl)triacetic acid (SCN-Bz-NOTA, 55 mg, 0.0982 mmol), and trimethylamine (0.068 mL, 0.491 mmol) prepared in step 3 were dissolved in chloroform (1.0 mL), followed by stirring at room temperature overnight. Upon completion of the reaction, the solvent was dried under reduced pressure. A product was confirmed by LC/MC.

Mass Spectrum (ESI$^+$), m/z=939 [M+H]$^+$.

Step 5: Preparation of (S)-2-(3-((S)-1-carboxy-5-(3-(4-((1,4,7-tris(carboxymethyl)-1,4,7-triazonane-2-yl)methyl)phenyl)thioureido)pentyl)ureido)pentanedioic acid

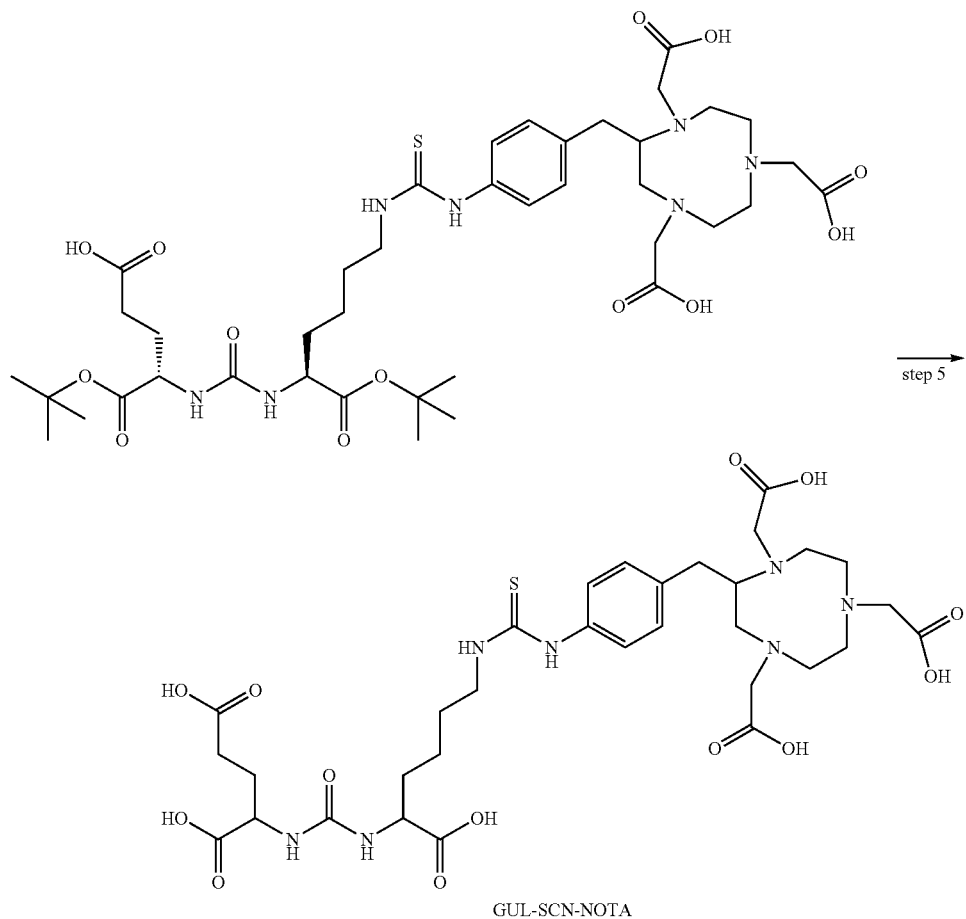

GUL-SCN-NOTA 2,2',2''-(2-(4-(3-((S)-6-(tert-butoxy)-5-(3-((S)-1,5-di-tert-butoxy-1,5-dioxopentane-2-yl)ureido)-6-oxohexyl)thioureido)benzyl)-1,4,7-triazonane-1,4,7-trityl)triacetic acid prepared in step 4 was dissolved in trifluoroacetic acid/dichloromethane (v/v 1/1, 2.0 mL), followed by stirring at room temperature for 4 hours. The mixture was dried under reduced pressure, followed by purification by HPLC using MeCN and distilled water to give GUL-NOTA.

Yield: 47.8 mg, 63% (2 steps overall yield).

$^1$H-NMR (DMSO-d$_6$, 600 MHz) δ 12.4 (br, 6H), 9.45 (s, 1H), 7.69 (s, 1H), 7.38 (d, J=8.10 Hz, 2H), 7.18 (d, J=8.16 Hz, 2H), 6.76~6.41 (br, 2H), 6.30 (m, 2H), 4.12-2.61 (m, 22H), 2.19 (m, 2H), 1.86 (m, 1H), 1.74-1.51 (m, 4H), 1.29 (m, 2H): Mass spectrum (ESI$^+$), m/z=770 [M+H]+.

Example 2: Preparation of Ga-NOTA-SCN-GUL

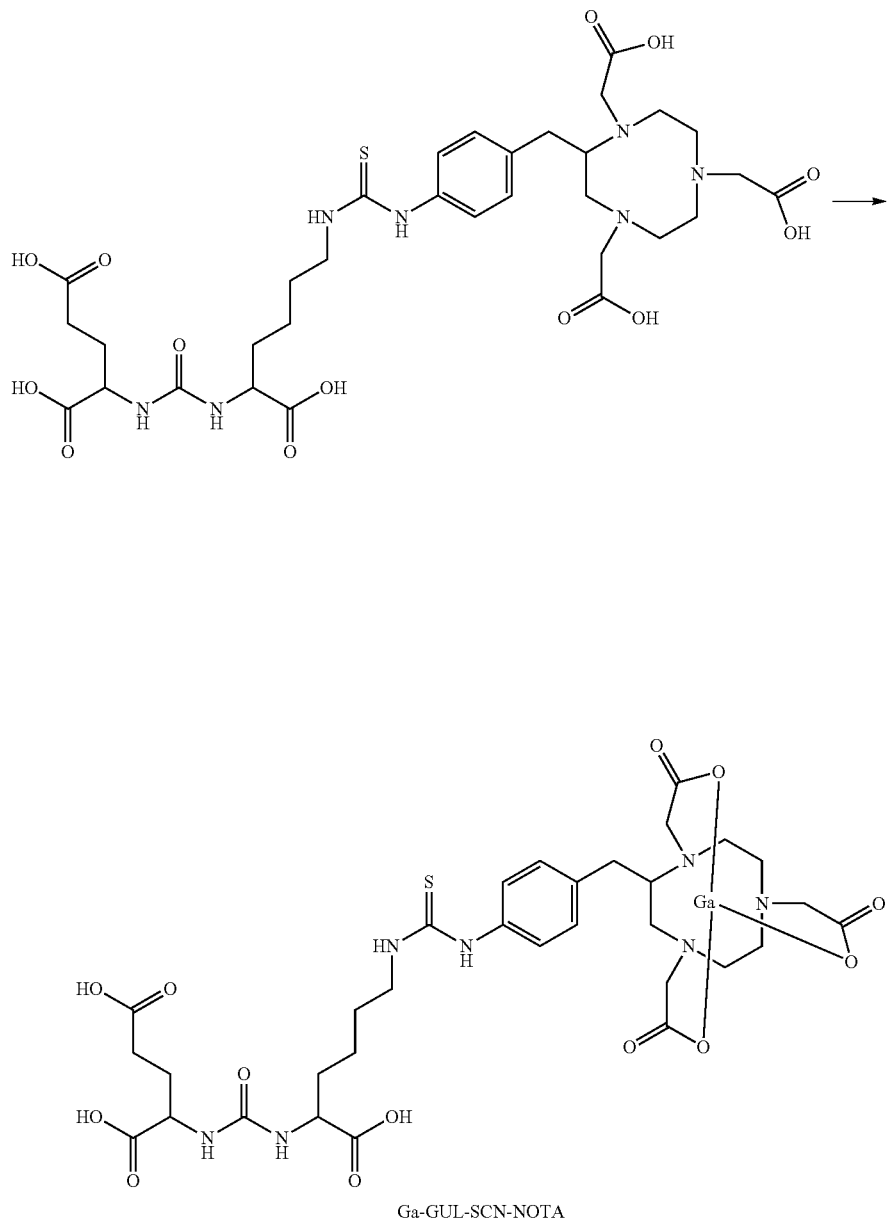

Ga-GUL-SCN-NOTA

GUL-NOTA (47.8 mg, 0.0621 mmol) prepared in Example 1 was dissolved in 1.0 M NaOAc buffer (2.0 mL, pH 5.6) together with 0.5 M $GaCl_3$ (1.242 mL, 0.621 mmol) dissolved in pentane, followed by stirring at room temperature for 8 hours. The reaction mixture was filtered through a 0.2 μm syringe filter, and the filtrate was separated by silica gel column chromatography (ethylacetate: n-hexane=1:1, v/v). As a result, a white solid compound was obtained.

Yield: 268 mg, 58%.

$^1$H-NMR (DMSO-$d_6$, 600 MHz) δ 12.4 (br, 3H), 9.45 (s, 1H), 7.69 (s, 1H), 7.38 (d, J=8.10 Hz, 2H), 7.18 (d, J=8.16 Hz, 2H), 6.76~6.41 (br, 2H), 6.30 (m, 2H), 4.12-2.61 (m, 22H), 2.19 (m, 2H), 1.89 (m, 1H), 1.74-1.51 (m, 4H), 1.29 (m, 2H): Mass spectrum (ESI$^+$), m/z=837 [M+H]$^+$.

Example 3: Preparation of Ga-68-NOTA-SCN-GUL

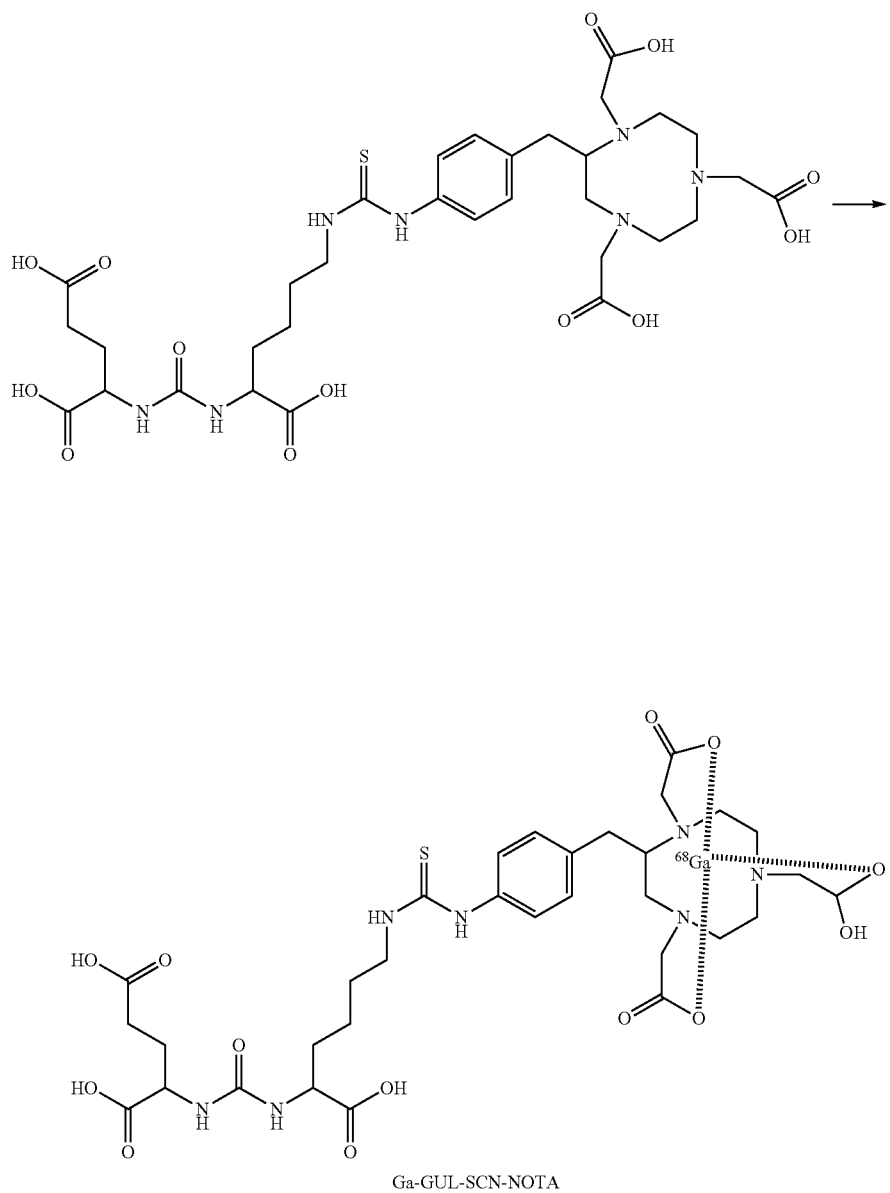

Ga-GUL-SCN-NOTA

Ga-68-Cl$_3$ (200 µL, 111 MBq) was dissolved in 0.1 M HCl, which was added to 1 M sodium acetate buffer (pH=5.6, 200 µL). MeCN solution containing GUL-NOTA (10 µL, 1 mg/mL) prepared in Example 1 was added thereto, which was vigorously stirred for 1 minute, followed by reaction at room temperature for 10 minutes. The labeling efficiency was calculated by performing ITLC-SG using 0.1 M Na$_2$CO$_3$ as a developing solvent. At this time, the labeled Ga-68-NOTA-SCN-GUL moved to the top (Rf=1.0) (FIG. 1a) and the unlabeled Ga-68 remained at the origin (Rf=0.0) (FIG. 1b). As a result, the labeling efficiency was more than 99%.

Example 4: Preparation of (S)-2-(3-((S)-1-carboxy-5-(3-(4-((1,4,7,10-tetrakis(carboxymethyl)-1,4,7,10-tetraazacyclododecane-2-yl)methyl)phenyl)thioureido)pentyl)ureido)pentanedioic acid (GUL-SCN-DOTA)

Step 1: Preparation of 2,2',2''-(2-(4-(3-((S)-6-(tert-butoxy)-5-(((S)-1,5-di-tert-butoxy-1,5-dioxopentane-2-yl)ureido)-6-oxohexyl)thioureido)benzyl)-1,4,7,10-tetraazacyclododecane-1,4,7,10-tetriyl) tetraacetic acid

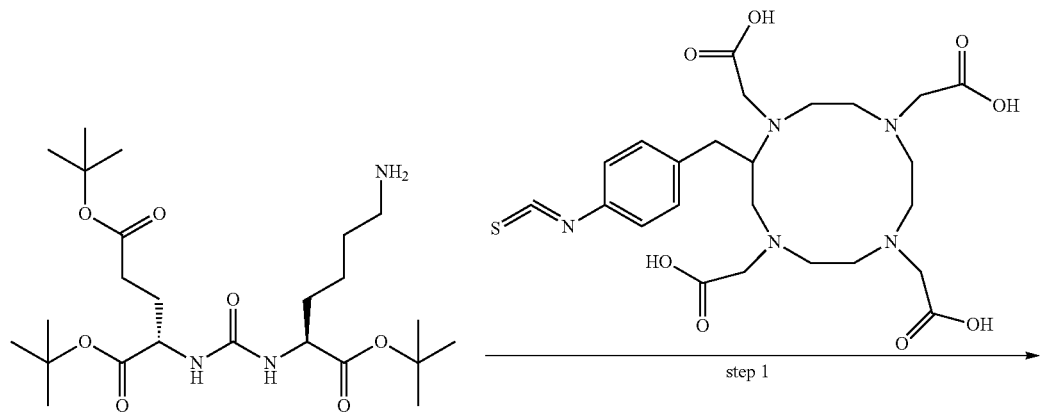

step 1

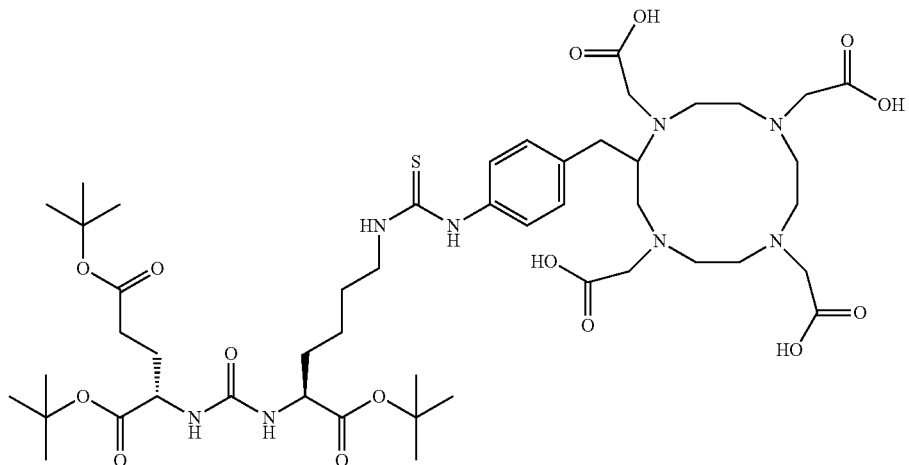

(S)-di-tert-butyl 2-(3-((S)-6-amino-1-tert-butoxy-1-oxo-hexan-2-yl)ureido)pentanedioate (30 mg, 0.0615 mmol) prepared in step 3 of Example 1,2,2',2',2'''-(2-(4-isothiocyanatobenzyl)-1,4,7,10-tetraazacyclododecane-1,4,7,10-tetrayl) tetraacetic acid(SCN-Bz-DOTA, 50 mg, 0.0727 mmol), and trimethylamine (0.043 mL, 0.308 mmol) were dissolved in chloroform (1.0 mL), followed by stirring at room temperature. The solvent was dried under reduced pressure and the molecular weight of the final product was calculated by LC/MS.

Mass spectrum (ESI$^+$), m/z=1040 [M+H]$^+$ observed.

Step 2: Preparation of (S)-2-(3-((S)-1-carboxy-5-(3-(4-((1,4,7,10-tetrakis(carboxymethyl)-1,4,7,10-tetraazacyclododecane-2-yl)methyl)phenyl)thioureido)pentyl)ureido)pentanedioic acid

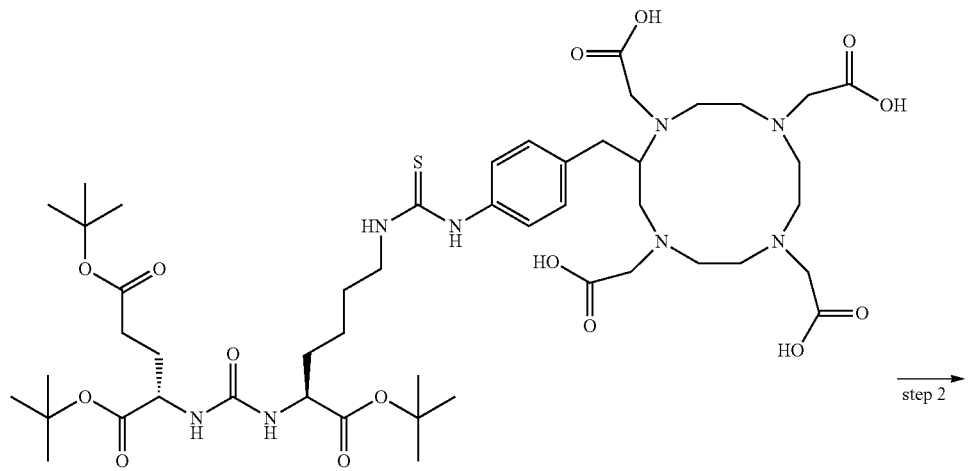

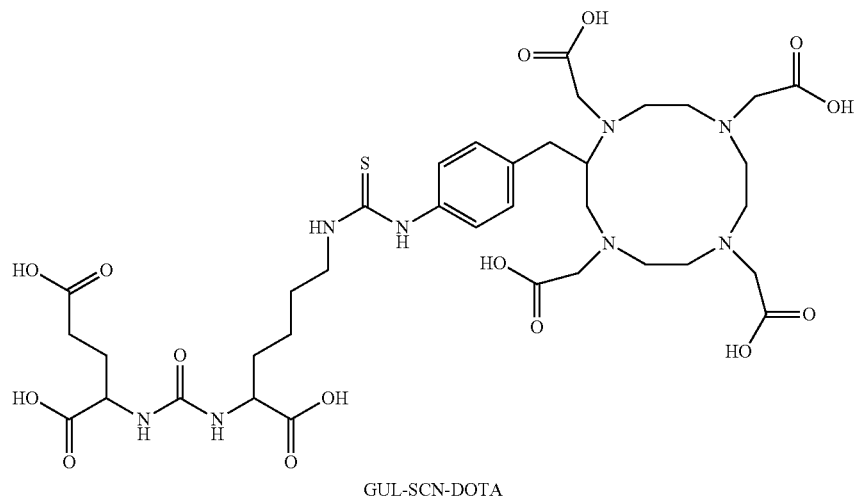

GUL-SCN-DOTA 2,2',2''-(2-(4-(3-((S)-6-(tert-butoxy)-5-(3-((S)-1,5-di-tert-butoxy-1,5-dioxopentane-2-yl)ureido)-6-oxohexyl)thioureido)benzyl)-1,4,7,10-tetraazacyclododecane-1,4,7,10-tetriyl)tetraacetic acid prepared in step 1 was dissolved in 2.0 mL of TFA/DCM (v/v: 1/1) solution, followed by stirring at room temperature for 4 hours. Upon completion of the reaction, the reaction mixture was dried under reduced pressure. The product was washed with DC containing 10% MeOH and as a result GUL-DOTA was obtained as a white powder with the yield of 43%. The molecular weight of the product was calculated by LC/MS.

Mass spectrum (ESI$^+$), m/z=871 [M+H]$^+$ observed.

Example 5: Preparation of Ga-68-DOTA-SCN-GUL

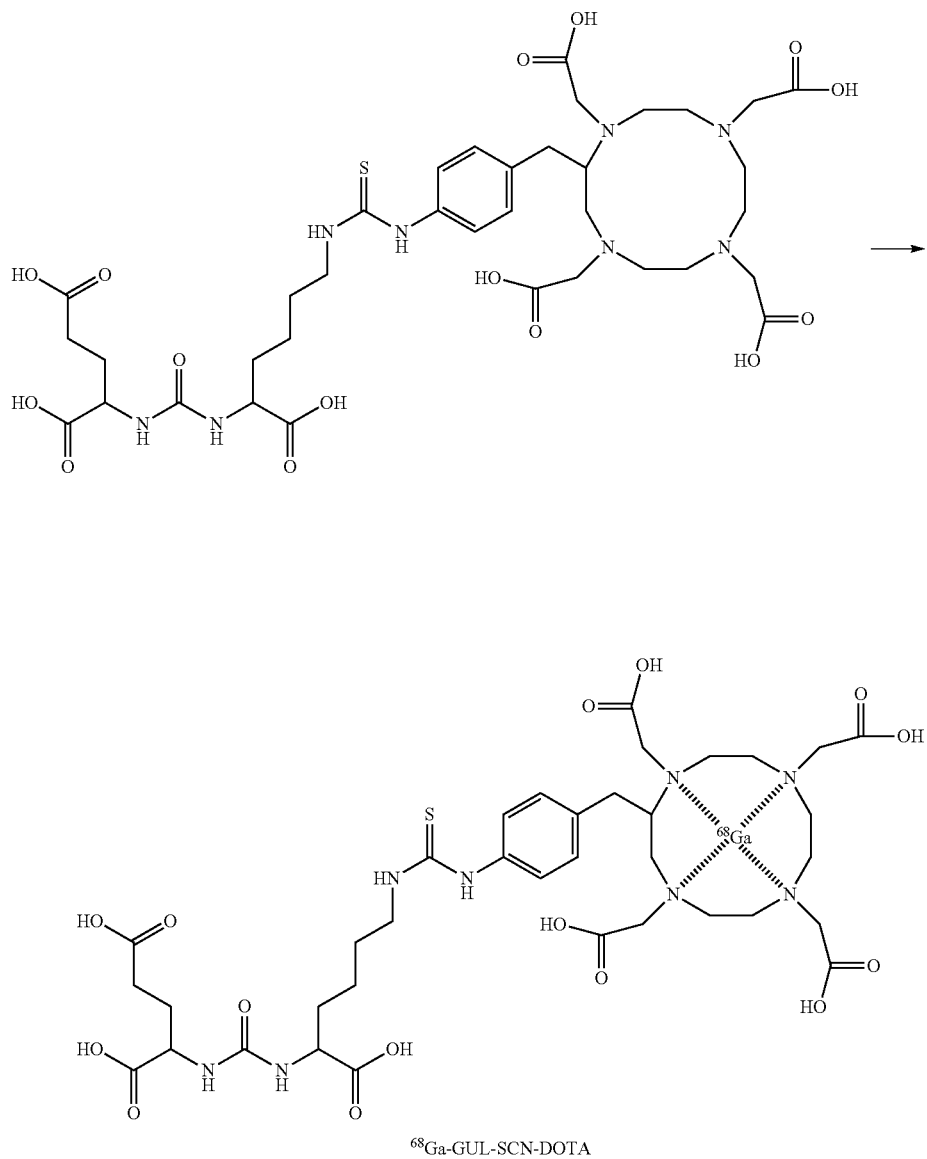

$^{68}$Ga-GUL-SCN-DOTA

MeCN solution containing GUL-DOTA (10 μL, 1 mg/mL) prepared in Example 4 was added thereto, which was vigorously stirred for 1 minute, followed by reaction at 95° C. for 10 minutes. The labeling efficiency was calculated by performing ITLC-SG using 0.1 M Na$_2$CO$_3$ as a developing solvent. At this time, the labeled Ga-68-DOTA-SCN-GUL moved to the top (Rf=1.0) (FIG. 2a) and the unlabeled Ga-68 remained at the origin (Rf=0.0) (FIG. 2b). As a result, the labeling efficiency was more than 95%.

DESCRIPTION OF THE PREFERRED EMBODIMENTS

Hereinafter, the present invention is described in detail.

The present invention provides the compound represented by formula 1 below or the pharmaceutically acceptable salt of the same.

[Formula 1]

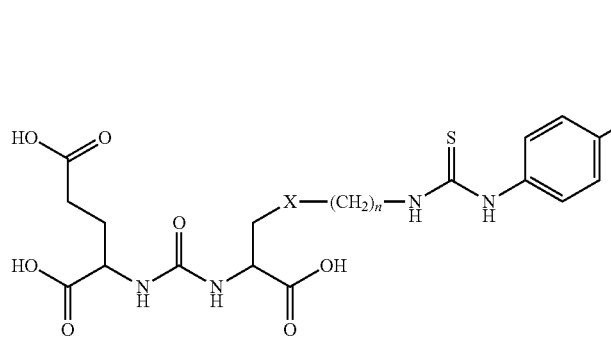

In formula 1,
X is single bond, —O— or —S—;
n is an integer of 1~5;
Y is —N(CH$_2$COOH) (CH$_2$)$_a$CH$_2$CH$_2$—,
m is an integer of 1 or 2; and
a, b and c are independently an integer of 0 or 1.

The compound represented by formula 1 of the present invention has the structure wherein a peptide ligand binding to PSMA (Prostate Specific Membrane Antigen) expressed specifically in prostate cancer binds to a bifunctional chelating agent suitable for labeling with a radio-isotope through a linker that is not hydrolyzed by protease without amide bond.

The peptide ligand above is not particularly limited as long as it is a ligand capable of binding to PSMA expressed specifically in prostate cancer. However, glutamic acid-urea-lysine, glutamic acid-urea-cysteine, or glutamic acid-urea-serine is preferably used herein.

The bifunctional chelating agent is not particularly limited as long as it is a substance capable of labeling a radio-isotope. Herein,

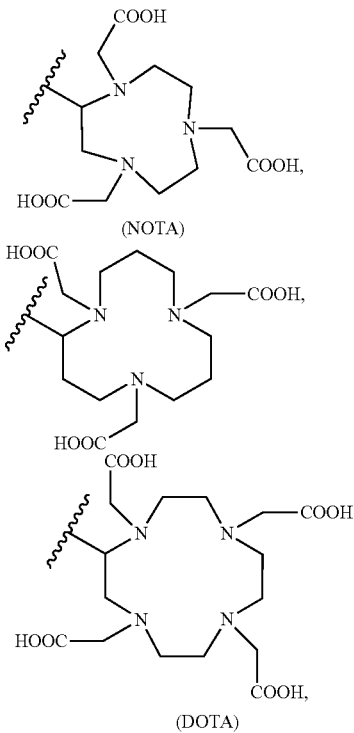

(NOTA)

(DOTA)

-continued

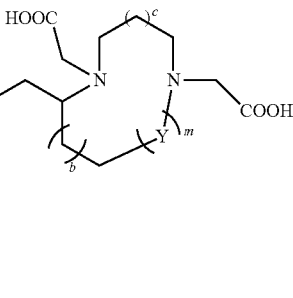

, or

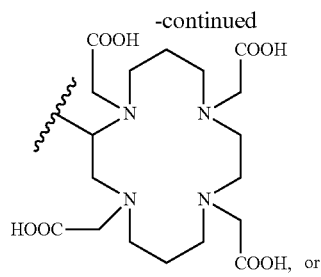

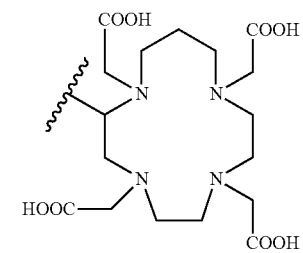

is preferably used and NOTA (1,4,7-triazacyclononane-1,4,7-triacetic acid) or DOTA (1,4,7,10-tetraazacyclododecane-1,4,7,10-tetraacetic acid) is more preferred.

The peptide thiourea derivative represented by formula 1 of the present invention can be preferably exemplified by the following compounds:

(1) 2-(3-(1-carboxy-5-(3-(4-((1,4,7-tris(carboxymethyl)-1,4,7-triazonane-2-yl)methyl)phenyl)thioureido)phenyl)ureido)pentanedioic acid (GUL-SCN-NOTA); and (2) 2-(3-(1-carboxy-5-(3-(4-((1,4,7,10-tetrakis(carboxymethyl)-1,4,7,10-tetraazacyclododecane-2-yl)methyl)phenyl)thioureido)pentyl)ureido)pentanedioic acid (GUL-SCN-DOTA).

The compound represented by formula 1 of the present invention can be used as the form of a pharmaceutically acceptable salt, in which the salt is preferably acid addition salt formed by pharmaceutically acceptable free acids. Herein, the pharmaceutically acceptable salt indicates any organic or inorganic addition salt of the base compound represented by Formula 1 that is relatively nontoxic to a patient and has non-harmful activity whose side effect cannot reduce any positive effect of the said base compound represented by formula 1. Whether it is inorganic or organic, a free acid can be used if it is pharmaceutically acceptable. Examples of the inorganic free acid include hydrochloric acid, bromic acid, nitric acid, sulfuric acid, perchloric acid, and phosphoric acid. Available organic free acids are exemplified by citric acid, acetic acid, lactic acid, malic acid, fumaric acid, gluconic acid, succinic acid, tartaric acid, galacturonic acid, embonic acid, glutamic acid, aspartic acid, oxalic acid, (D) or (L) malic acid, maleic acid, methanesulfonic acid, ethanesulfonic acid, 4-toluenesulfonic acid, salicylic acid, citric acid, benzoic acid, and malonic acid. The salt herein also includes alkali metal salts (sodium salt, potassium salt, etc) and alkali earth metal salts (calcium salt, magnesium salt, etc). For example, as acid addition salts, acetate, aspartate, benzate, besylate, bicarbonate/carbonate, bisulfate/sulfate, borate, camcilate, citrate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maliate, malonate, methylate, methylsulfate, naphthylate, 2-naphsilate, nicothinate, nitrate, orotate, oxalate, palmitate, pamotate, phosphate/hydrogen phosphate/dihydrogen phosphate, saccharate, stearate, succinate, tartrate, tosylate, trifluoroacetate, aluminum, arginine, benzathine, calcium, choline, diethylamine, diolamine, glycine, lysine, magnesium, meglumine, olamine, potassium, sodium, tromethamine, and zinc salt can be included. Among them, hydrochloride or trifluoroacetate is preferred.

The compound represented by formula 1 of the present invention includes not only pharmaceutically acceptable salts, but also all salts, isomers, hydrates, and solvates which can be prepared by the conventional method.

The addition salt in this invention can be prepared by the conventional method known to those in the art. For example, the compound of formula 1 is dissolved in water-miscible organic solvent such as acetone, methanol, ethanol, or acetonitrile, to which excessive organic acid or acid aqueous solution of inorganic acid is added to induce precipitation or crystallization. Then, the solvent or the excessive acid is evaporated from the mixture, followed by drying the mixture to give addition salt or suction-filtering the precipitated salt to give the same.

The present invention also provides a preparation method of the compound represented by formula 1 comprising the step of preparing the compound represented by formula 1 by reacting the compound represented by formula 2 and the compound represented by formula 3 (step 1), as shown in reaction formula 1 below.

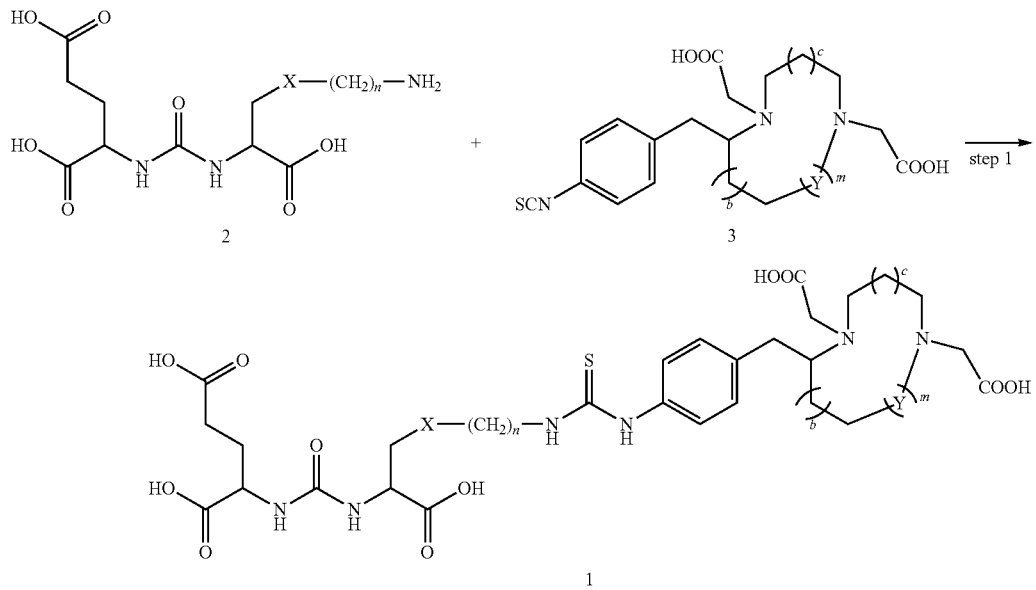

[Reaction Formula 1]

In reaction formula 1,

X, n, Y, m, a, b, and c are as defined in formula 1.

Hereinafter, the preparation method of the present invention is described in more detail.

According to the preparation method of the present invention, the compound represented by formula 1 is prepared by reacting amine group (—NH$_2$) of the compound represented by formula 2 which is the peptide derivative with isothiocyanate (—N=C=S) of the compound represented by formula 3 in the presence of a base.

If the end of the peptide derivative moiety bound to PSMA expressed in prostate cancer is —OH or —SH, a step of introducing C$_1$~C$_5$ alkylamine moiety can be additionally performed.

At this time, the base herein is exemplified by organic bases such as triethylamine (TEA), N,N-diisopropylethylamine (DIPEA), 1,8-diazabicyclo[5.4.0]'-7-undesene (DBU), and pyridine; or inorganic bases such as sodium t-butoxide, potassium t-butoxide, sodium hydroxide, sodium carbonate, potassium carbonate, cesium carbonate, and sodium hydride. The base can be used in equivalent amounts or in excess, alone or in combination, but not always limited thereto.

The reaction solvent used herein is exemplified by chloroform, dimethyl formamide (DMF), toluene, dimethylacetamide (DMA), dimethylsulfoxide (DMSO), methylenechloride, dichloroethane, water, ethylacetate, acetonitrile; lower alcohols including isopropanol, methanol, ethanol, propanol and butanol; and ether solvents including tetrahydrofuran (THF), dioxane, ethylether and 1,2-dimethoxyethane. The solvents above can be used independently or in combination. Further, the reaction temperature is preferably room temperature but can be adjusted according to the progress of the reaction, and not limited thereto.

According to the preparation method of the present invention, the compound represented by formula 1 can be easily prepared by reacting amine group (—$NH_2$) at the end of the peptide derivative and isothiocyanate of the bifunctional chelating agent directly in a single step under the mild condition.

In addition, the present invention provides a labeled compound prepared by coordinating a metallic radio-isotope to the compound represented by formula 1 above or the pharmaceutically acceptable salt thereof.

The metallic radio-isotope herein is preferably $^{67}$Ga, $^{68}$Ga, $^{62}$Cu, $^{64}$Cu, $^{67}$Cu, $^{111}$In, $^{90}$Y, $^{177}$Lu, or $^{117m}$Sn.

The metallic radio-isotope is labeled with high efficiency when a protein is labeled with a positron emission nuclide produced in a generator using a bifunctional chelating agent, in particular

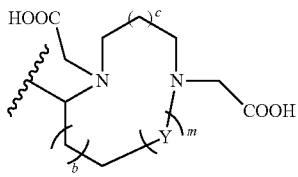

(Y, m, b, and c are as defined as formula 1) of the compound represented by formula of the present invention, as a mediator.

The labeled compound of the present invention contains a linker that is not hydrolyzed by protease in serum in vivo, so that it displays excellent stability in human serum, indicating that the compound can be effectively used as a labeled compound (see Experimental Example 1).

The present invention also provides a pharmaceutical composition for treating or diagnosing prostate cancer comprising the labeled compound above as an active ingredient. In addition, the present invention provides a radiopharmaceutical for imaging prostate cancer comprising the labeled compound above as an active ingredient.

At this time, the radio-isotopes are mainly alpha-ray emitting radionuclides, beta-ray emitting radionuclides, gamma-ray emitting radionuclides, and positron-beam emitting radionuclides, etc. Among them, alpha-ray emitting radionuclides and beta-ray emitting radionuclides are used for the treatment and gamma-ray emitting radionuclides and positron-beam emitting radionuclides are used for the diagnosis by nucleus imaging.

When the pharmaceutical composition of the present invention is used for imaging prostate cancer, the radio-isotope of the labeled compound is preferably $^{67}$Ga, $^{68}$Ga, $^{62}$Cu, $^{64}$Cu, $^{67}$Cu, or $^{111}$In. When the pharmaceutical composition of the present invention is used for treating prostate cancer, the radio-isotope is preferably $^{64}$Cu, $^{67}$Cu, $^{90}$Y, $^{177}$Lu, or $^{117m}$Sn.

Among the radio-isotopes, Ga-68 is a well known positron-beam emitting radionuclide, which has as short half-life as 68 minutes. So, it is useful for PET and particularly it has a great potential for future use because of economical advantage due to the development of a generator. Ga-68 is mostly labeled with DOTA (1,4,7,10-tetraazacyclododecane-1,4,7,10-tetraacetic acid) or NOTA (1,4,7-triazacyclononane-1,4,7-triacetic acid) as a bifunctional chelating agent.

DOTA is widely used for labeling of such radio-isotopes as In-111, Y-90, Lu-177, and Ga-68. NOTA is used to label In-111 and Ga-67 with T101, a monoclonal antibody, which is unstable with In-111, but is stably labeled with Ga-67 (Lee J, et el. Nucl Med Biol 1997; 24:225-30).

The pharmaceutical composition of the present invention is excellent in stability in human serum when it is administered in vivo and is not only excellent in binding to PSMA expressed competitively in prostate cancer but also excellent in suppressing PSMA at a low concentration. The composition is excreted into the kidney rather than the bile passage because of its high water-solubility. So, the composition can be absorbed in prostate cancer tissues and emits radiation to the prostate cancer region. Therefore, the composition of the invention can be effectively used as a pharmaceutical composition for treating and diagnosing prostate cancer.

Further, the present invention provides a kit for treating or diagnosing prostate cancer comprising the compound represented by formula 1 above or the pharmaceutically acceptable salt thereof and labeled with a pharmaceutically acceptable metallic radio-isotope in a non-pyrogenic sterilized form.

Particularly, the kit for treating or diagnosing prostate cancer of the present invention contains the compound represented by formula 1 at the concentration of 10 ng~100 mg.

The kit for treating or diagnosing prostate cancer of the present invention comprises the sterilized vial containing the compound represented by formula 1 in a proper buffer in order for the compound represented by formula 1 to be easily labeled with a metallic radio-isotope which is stored as sealed in a refrigerator, a freezer or freeze-dried, and then used as needed.

At this time, to regulate pH in the course of radio-isotope labeling, 0.01 mL 1~0 mL of a buffer (pH 1~9, conc. 1 μM~10 M) was added thereto, which can be sealed in the dissolved state, frozen state or freeze-dried state.

The buffer herein is preferably acetic acid, phosphoric acid, citric acid, fumaric acid, ascorbic acid, butyric acid, succinic acid, tartaric acid, carbonic acid, glucoheptonic acid, gluconic acid, glucuronic acid, glucaric acid, boric acid or their sodium salts or potassium salts.

In addition, the kit of the present invention can additionally contain an antioxidant. The antioxidant is to prevent degradation of the compound represented by formula 1 labeled with a radio-isotope caused by radiation decomposition, which is preferably exemplified by vitamin C or gentisic acid. The antioxidant is preferably contained in the kit of the present invention in an amount of 0~500 mg per unit dose.

The kit can be supplemented with buffer sterilization vials, saline, syringes, filters, columns, and other ancillary equipments to produce injectable drugs for use by medical technologists or technicians. It is well known to those in the art who have general knowledge on this field that the kit can be varied or modified according to the personal need or diet of a patient and also can be changed in the manner where the radio-isotope is provided or obtained.

The kit above can provide a radio-isotope labeled compound by adding a radio-isotope to the compound represented by formula 1 at the concentration of 0.1~500 or 1~500 mCi per 1 mg of the compound, followed by reaction for 0.1~30 minutes right before use.

Practical and presently preferred embodiments of the present invention are illustrative as shown in the following Examples.

However, it will be appreciated that those skilled in the art, on consideration of this disclosure, may make modifications and improvements within the spirit and scope of the present invention.

Example 1: Preparation of (S)-2-(3-((S)-1-carboxy-5-(3-(4-((1,4,7-tris(carboxymethyl)-1,4,7-triazonane-2-yl)methyl)phenyl)thioureido)pentyl)ureido)pentanedioic acid (GUL-SCN-NOTA)

Step 1: Preparation of (S)-di-tert-butyl 2-(1H-imidazole-1-carboxamido)pentanedioate

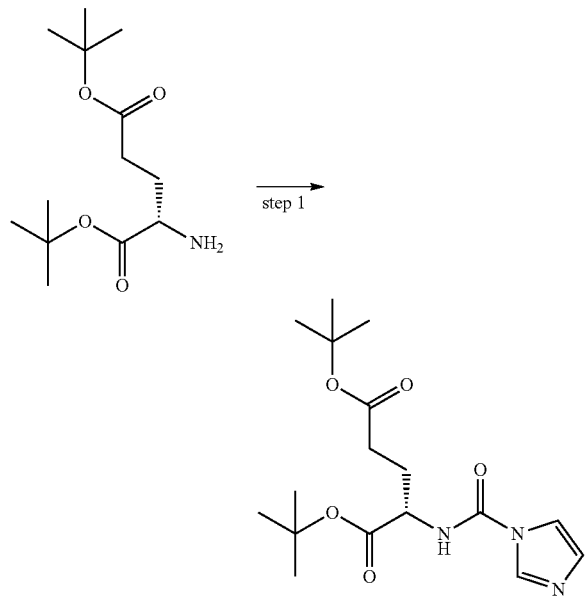

L-di-tert-butyl glutamate hydrochloride (1.50 g, 5.1 mmol) was dissolved in dichloromethane (15 mL) and then cooled to 0☐, to which triethylamine (1.74 mL, 12.5 mmol) and 4-(dimethylamino)pyridine were added. The mixture was stirred for 5 minutes, then 1,1'-carbonyldiimidazole (981 mg, 6.05 mmol) was added thereto. The temperature of the mixture was raised to room temperature, followed by stirring for 18 hours. 30 mL of dichloromethane was added thereto for the dilution. The mixture was washed with saturated sodium bicarbonate solution (10 mL), water (2×10 mL), and brine (10 mL). Then, the organic layer was dehydrated with sodium sulfate. The mixture was filtered and the filtrate was dried under reduced pressure, followed by the treatment of hexane/ethylacetate solution. As a result, a white solid material was obtained. The obtained white solid material was washed with hexane (50 mL) and the final white solid material was analyzed by instrumental analysis.

Yield: 1.44 g, 80%;

$^1$H-NMR (DMSO-$d_6$, 600 MHz) δ 8.29 (s, 1H), 7.73 (s, 1H), 7.05 (s, 1H), 7.01 (s, 1H), 4.24 (m, 1H), 2.36 (t, J=7.26 Hz, 2H), 2.03 (m, 1H), 1.87 (m, 1H), 1.42 (s, 9H), 1.39 (s, 9H).

Mass spectrum (ESI$^+$), m/z=354 [M+H]$^+$.

Step 2: Preparation of (9S,13S)-tri-tert-butyl 3,11-dioxo-1-phenyl-2-oxa-4,10,12-triazapentadekan-9,13,15-tricarboxylate

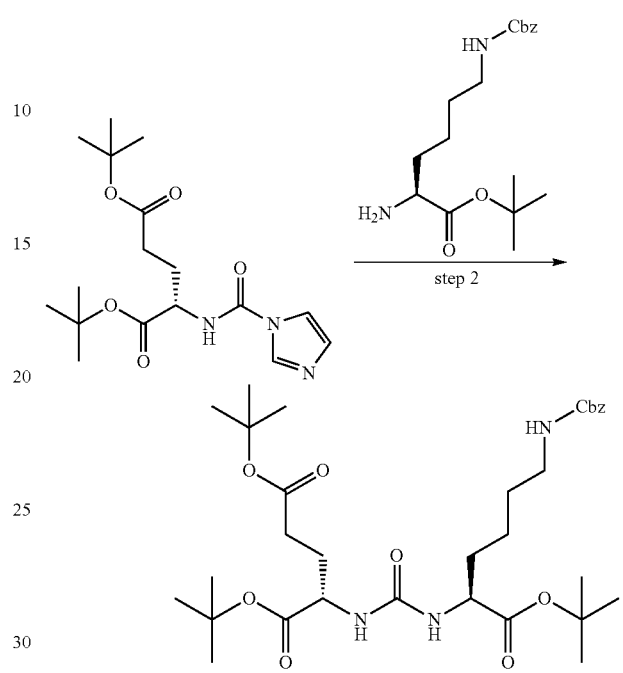

(S)-di-tert-butyl 2-(1H-imidazole-1-carboxamido)pentanedioate (780 mg, 2.208 mmol) prepared in step 1 was dissolved in dichloromethane (7.8 mL), and then cooled to 00, to which triethylamine (0.615 mL, 4.417 mmol) and methyl trifluoromethanesulfonate (MeOTf) (0.252 mL, 2.230 mmol) were added. The temperature of the mixture was raised to room temperature while stirring, followed by further stirring for 30 minutes at room temperature. The reaction mixture was added with (S)-tert-butyl 2-amino-6-(((benzyloxy)carbonyl)amino)hexanoate (743 mg, 2.208 mmol) and heated at 40☐, followed by stirring overnight. Upon completion of the reaction, the solution was dried under reduced pressure. Then, a solid product was obtained by using ether and hexane.

Yield: 1.18 g, 86%;

Mass spectrum (ESI$^+$), m/z=622 [M+H]$^+$.

Step 3: Preparation of (S)-di-tert-butyl 2-(3-((S)-6-amino-1-tert-butoxy-1-oxohexane-2-yl) ureido) pentanedioate

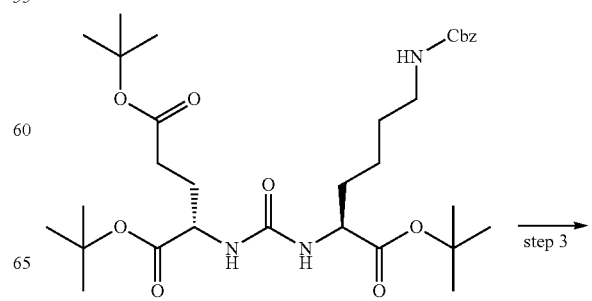

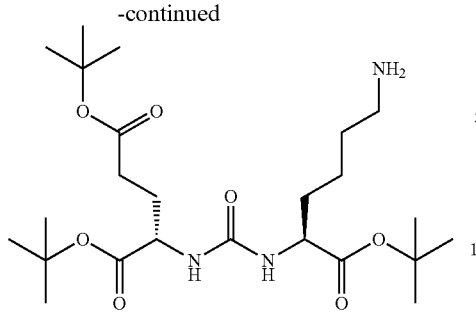

Ammonium formate (314 mg, 4.986 mmol) and 10 wt % palladium carbon (100 mg) were added to the (9S,13S)-tri-tert-butyl 3,11-dioxo-1-phenyl-2-oxa-4,10,12-triazapentadekan-9,13,15-tricarboxylate (310 mg, 0.499 mmol) ethanol (5 mL) solution prepared in step 2, followed by stirring at room temperature for 4 hours. Upon completion of the reaction, the mixture was filtered by using Celite 545 and then washed with ethylacetate (25 mL×3). A white solid product was obtained by distillating the filtrate under reduced pressure.

Yield: 243 mg, 98%.

$^1$H-NMR (DMSO-$d_6$, 600 MHz) δ 8.43 (s, 1H), 8.10-7.10 (br, 1H), 6.50 (m, 2H), 4.01 (m, 1H), 3.92 (m, 1H), 2.69 (m, 2H), 2.17 (m, 2H), 1.83 (m, 1H), 1.70-1.49 (m, 4H), 1.38 (m, 27H), 1.29 (m, 2H).

Mass spectrum (ESI$^+$), m/z=488 [M+H]$^+$.

Step 4: Preparation of 2,2',2''-(2-(4-(3-((S)-6-(tert-butoxy)-5-(3-((S)-1,5-di-tert-butoxy-1,5-dioxopentane-2-yl) ureido)-6-oxohexyl)thioureido)benzyl)-1,4,7-triazonane-1,4,7-trityl)triacetic acid

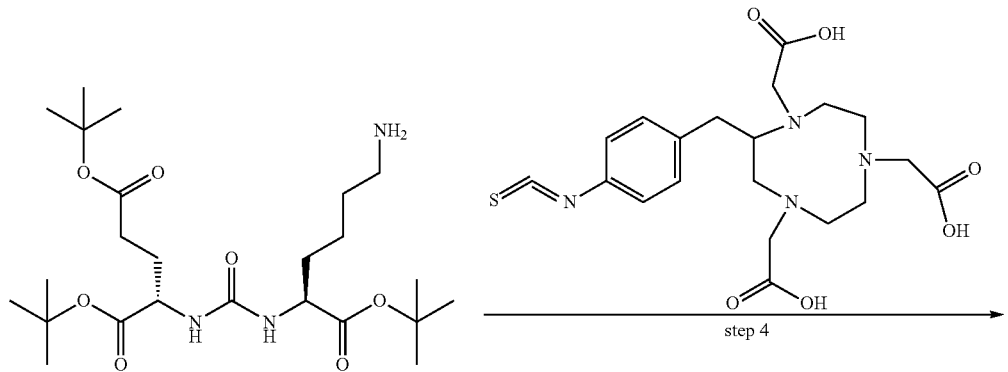

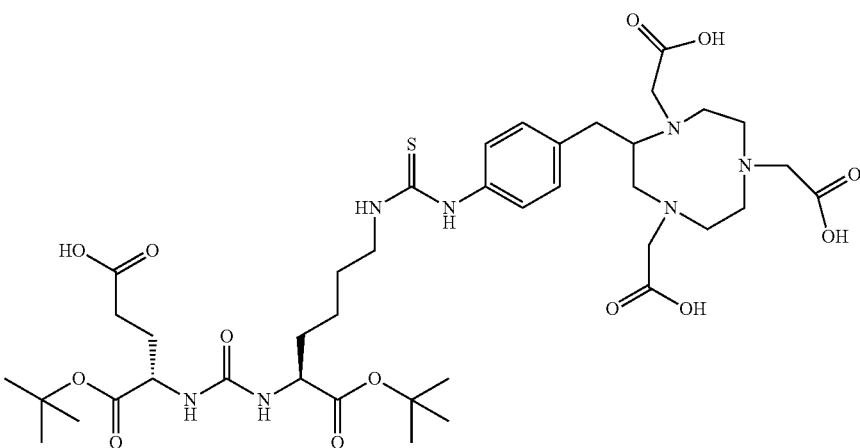

(S)-di-tert-butyl 2-(3-((S)-6-amino-1-tert-butoxy-1-oxo-hexane-2-yl)ureido)pentanedioate (47.8 mg, 0.0982 mmol), 2,2',2''-(2-(4-isothiocyanatobenzyl)-1,4,7-triazonane-1,4,7-triyl)triacetic acid (SCN-Bz-NOTA, 55 mg, 0.0982 mmol), and trimethylamine (0.068 mL, 0.491 mmol) prepared in step 3 were dissolved in chloroform (1.0 mL), followed by stirring at room temperature overnight. Upon completion of the reaction, the solvent was dried under reduced pressure. A product was confirmed by LC/MC.

Mass Spectrum (ESI$^+$), m/z=939 [M+H]$^+$.

Step 5: Preparation of (S)-2-(3-((S)-1-carboxy-5-(3-(4-((1,4,7-tris(carboxymethyl)-1,4,7-triazonane-2-yl)methyl)phenyl)thioureido)pentyl)ureido)pentanedioic acid

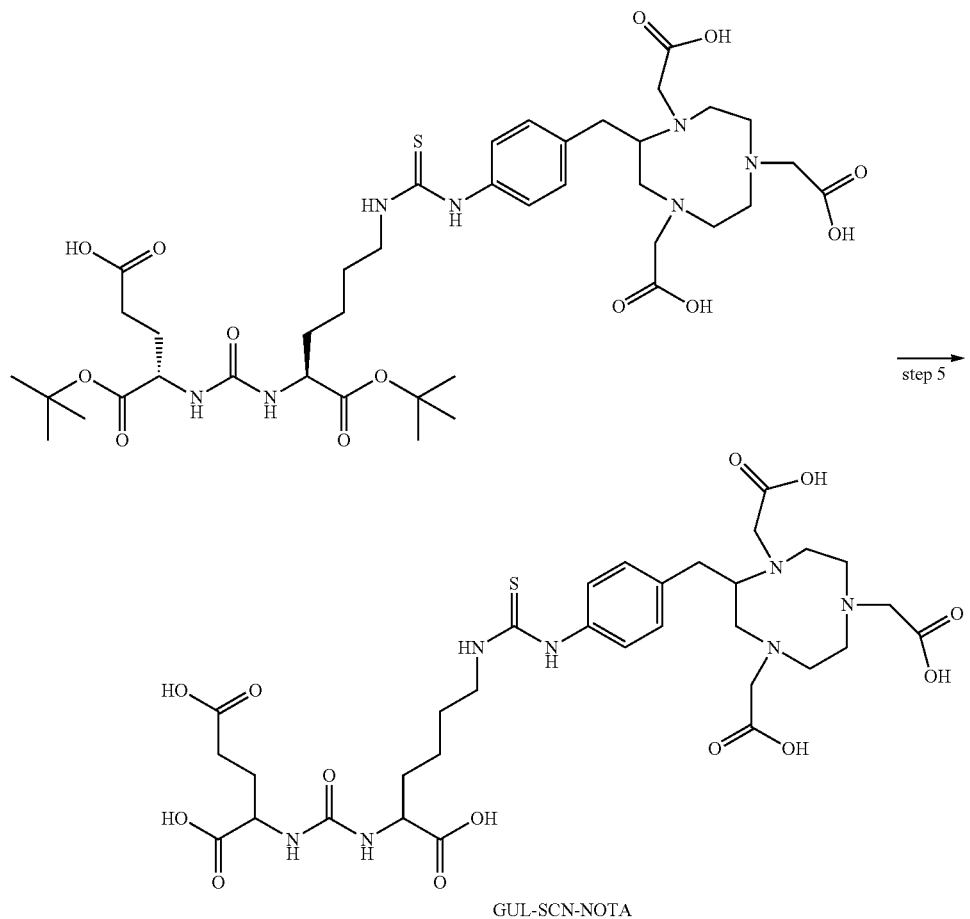

GUL-SCN-NOTA 2,2',2''-(2-(4-(3-((S)-6-(tert-butoxy)-5-(3-((S)-1,5-di-tert-butoxy-1,5-dioxopentane-2-yl)ureido)-6-oxohexyl)thioureido)benzyl)-1,4,7-triazonane-1,4,7-trityl)triacetic acid prepared in step 4 was dissolved in trifluoroacetic acid/dichloromethane (v/v 1/1, 2.0 mL), followed by stirring at room temperature for 4 hours. The mixture was dried under reduced pressure, followed by purification by HPLC using MeCN and distilled water to give GUL-NOTA.

Yield: 47.8 mg, 63% (2 steps overall yield).

$^1$H-NMR (DMSO-d$_6$, 600 MHz) δ 12.4 (br, 6H), 9.45 (s, 1H), 7.69 (s, 1H), 7.38 (d, J=8.10 Hz, 2H), 7.18 (d, J=8.16 Hz, 2H), 6.76~6.41 (br, 2H), 6.30 (m, 2H), 4.12-2.61 (m, 22H), 2.19 (m, 2H), 1.86 (m, 1H), 1.74-1.51 (m, 4H), 1.29 (m, 2H): Mass spectrum (ESI$^+$), m/z=770 [M+H]$^+$.

Example 2: Preparation of Ga-NOTA-SCN-GUL

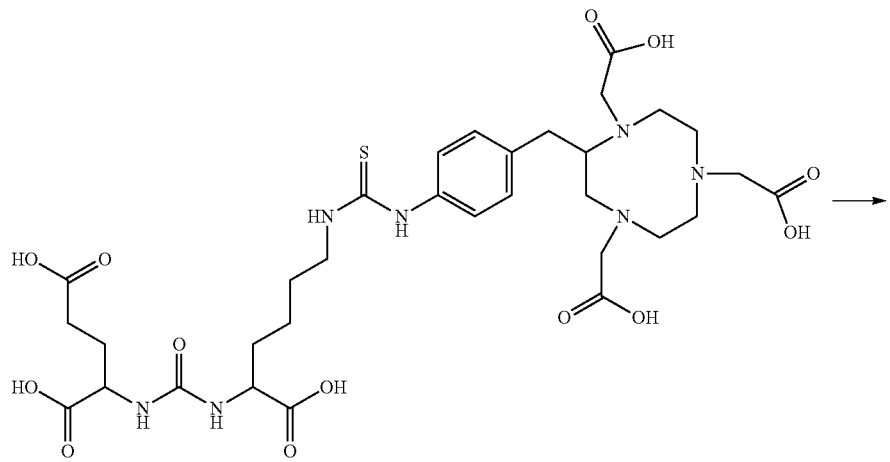

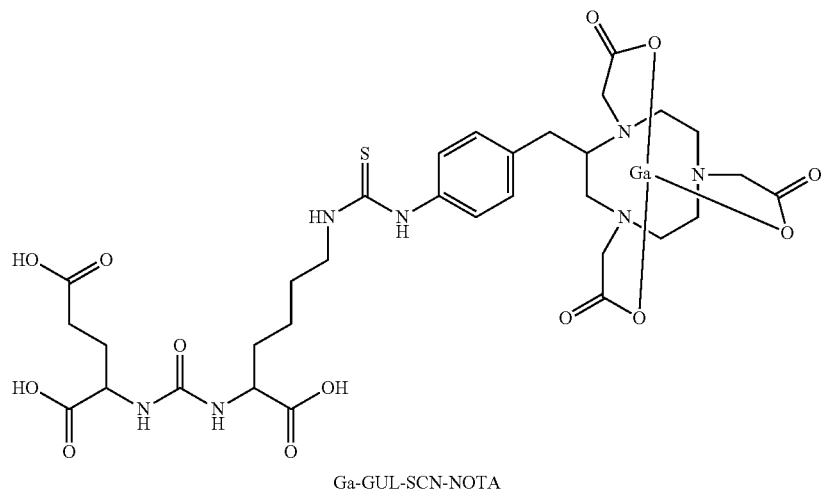

Ga-GUL-SCN-NOTA

GUL-NOTA (47.8 mg, 0.0621 mmol) prepared in Example 1 was dissolved in 1.0 M NaOAc buffer (2.0 mL, pH 5.6) together with 0.5 M GaCl$_3$ (1.242 mL, 0.621 mmol) dissolved in pentane, followed by stirring at room temperature for 8 hours. The reaction mixture was filtered through a 0.2 μm syringe filter, and the filtrate was separated by silica gel column chromatography (ethylacetate: n-hexane=1:1, v/v). As a result, a white solid compound was obtained.

Yield: 268 mg, 58%.

$^1$H-NMR (DMSO-d$_6$, 600 MHz) δ 12.4 (br, 3H), 9.45 (s, 1H), 7.69 (s, 1H), 7.38 (d, J=8.10 Hz, 2H), 7.18 (d, J=8.16 Hz, 2H), 6.76~6.41 (br, 2H), 6.30 (m, 2H), 4.12-2.61 (m, 22H), 2.19 (m, 2H), 1.89 (m, 1H), 1.74-1.51 (m, 4H), 1.29 (m, 2H): Mass spectrum (ESI$^+$), m/z=837 [M+H]+.

Example 3: Preparation of Ga-68-NOTA-SCN-GUL

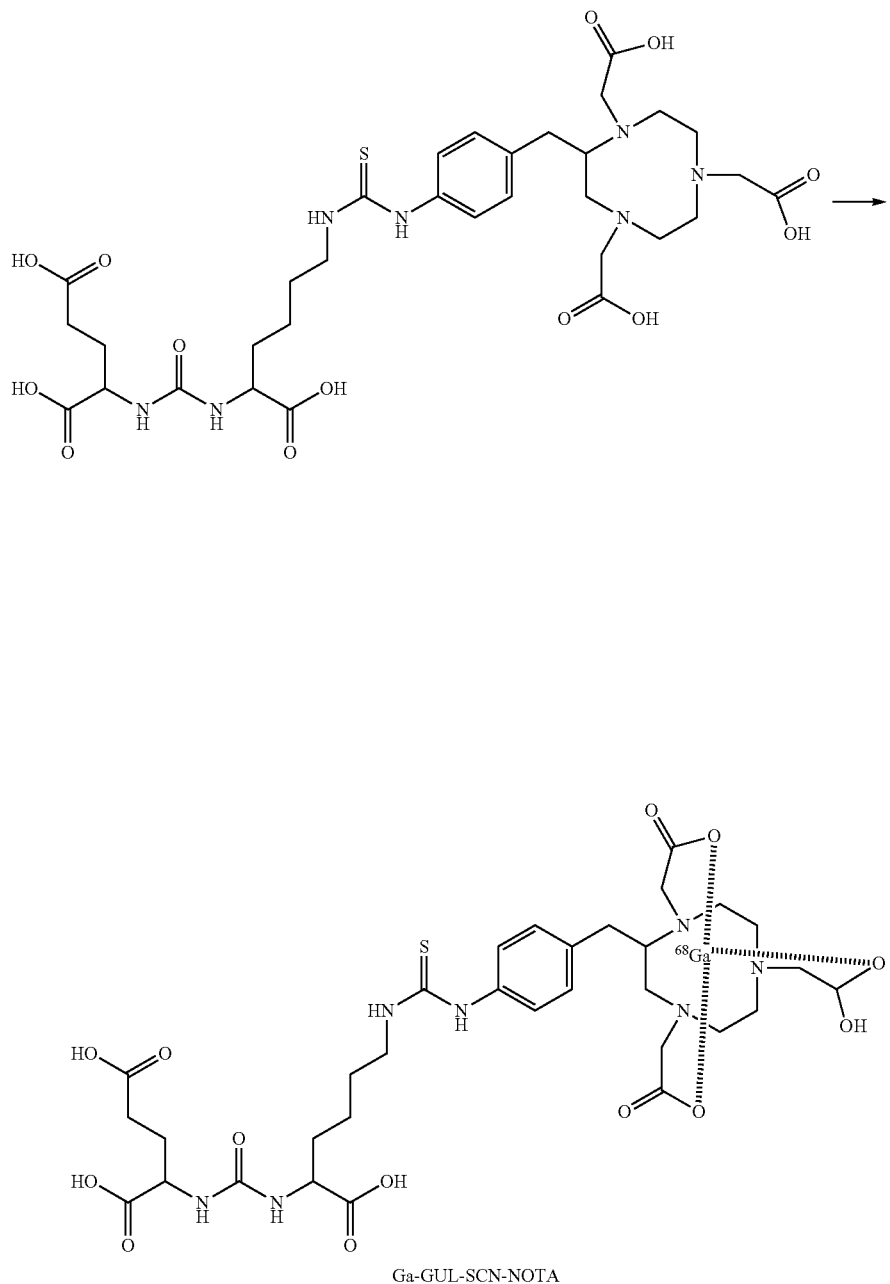

Ga-GUL-SCN-NOTA

Ga-68-Cl$_3$ (200 μL, 111 MBq) was dissolved in 0.1 M HCl, which was added to 1 M sodium acetate buffer (pH=5.6, 200 μL). MeCN solution containing GUL-NOTA (10 μL, 1 mg/mL) prepared in Example 1 was added thereto, which was vigorously stirred for 1 minute, followed by reaction at room temperature for 10 minutes. The labeling efficiency was calculated by performing ITLC-SG using 0.1 M Na$_2$CO$_3$ as a developing solvent. At this time, the labeled Ga-68-NOTA-SCN-GUL moved to the top (Rf=1.0) (FIG. 1a) and the unlabeled Ga-68 remained at the origin (Rf=0.0) (FIG. 1b). As a result, the labeling efficiency was more than 99%.

Example 4: Preparation of (S)-2-(3-((S)-1-carboxy-5-(3-(4-((1,4,7,10-tetrakis(carboxymethyl)-1,4,7,10-tetraazacyclododecane-2-yl)methyl)phenyl)thioureido)pentyl)ureido)pentanedioic acid (GUL-SCN-DOTA)

Step 1: Preparation of 2,2',2''-(2-(4-(3-((S)-6-(tert-butoxy)-5-(((S)-1,5-di-tert-butoxy-1,5-dioxopentane-2-yl)ureido)-6-oxohexyl)thioureido)benzyl)-1,4,7,10-tetraazacyclododecane-1,4,7,10-tetriyl)tetraacetic acid

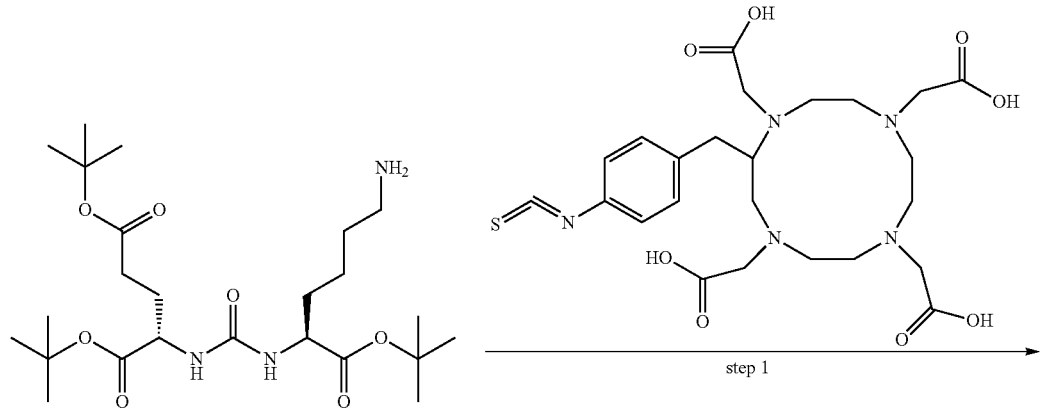

step 1

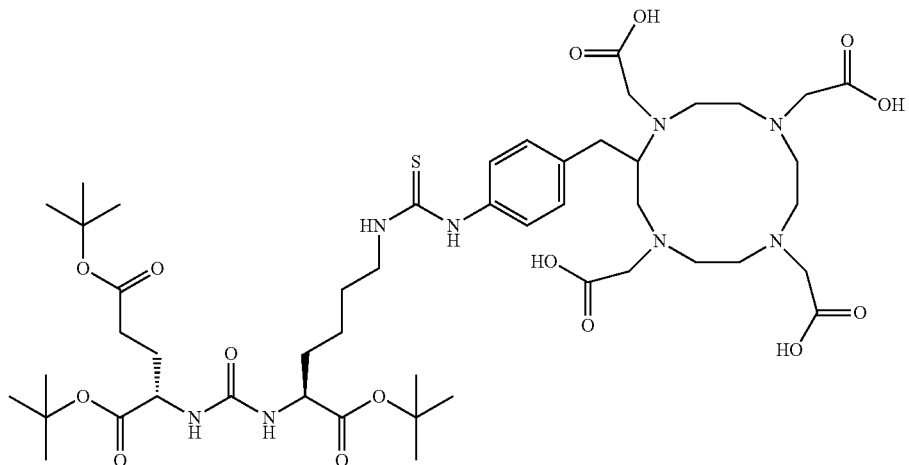

(S)-di-tert-butyl 2-(3-((S)-6-amino-1-tert-butoxy-1-oxohexan-2-yl)ureido)pentanedioate (30 mg, 0.0615 mmol) prepared in step 3 of Example 1,2,2',2'',2'''-(2-(4-isothiocyanatobenzyl)-1,4,7,10-tetraazacyclododecane-1,4,7,10-tetrayl)tetraacetic acid(SCN-Bz-DOTA, 50 mg, 0.0727 mmol), and trimethylamine (0.043 mL, 0.308 mmol) were dissolved in chloroform (1.0 mL), followed by stirring at room temperature. The solvent was dried under reduced pressure and the molecular weight of the final product was calculated by LC/MS.

Mass spectrum (ESI$^+$), m/z=1040 [M+H]$^+$ observed.

Step 2: Preparation of (S)-2-(3-((S)-1-carboxy-5-(3-(4-((1,4,7,10-tetrakis(carboxymethyl)-1,4,7,10-tetraazacyclododecane-2-yl)methyl)phenyl)thioureido)pentyl)ureido)pentanedioic acid

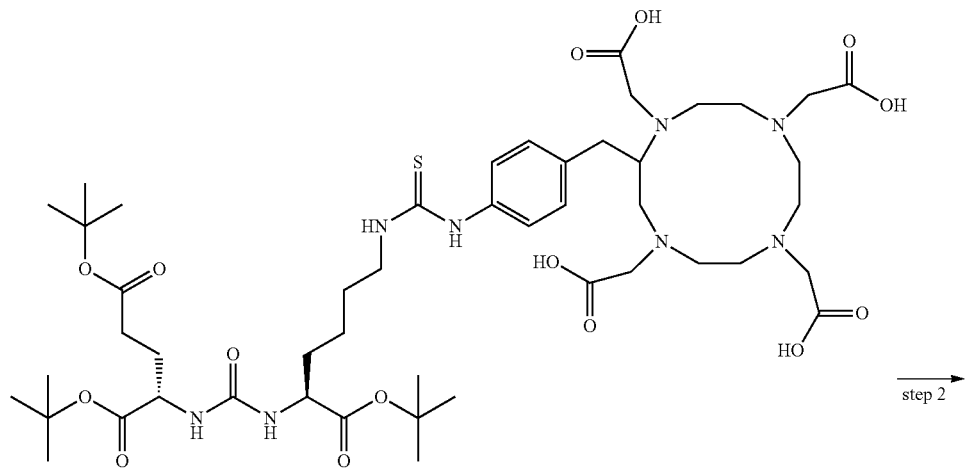

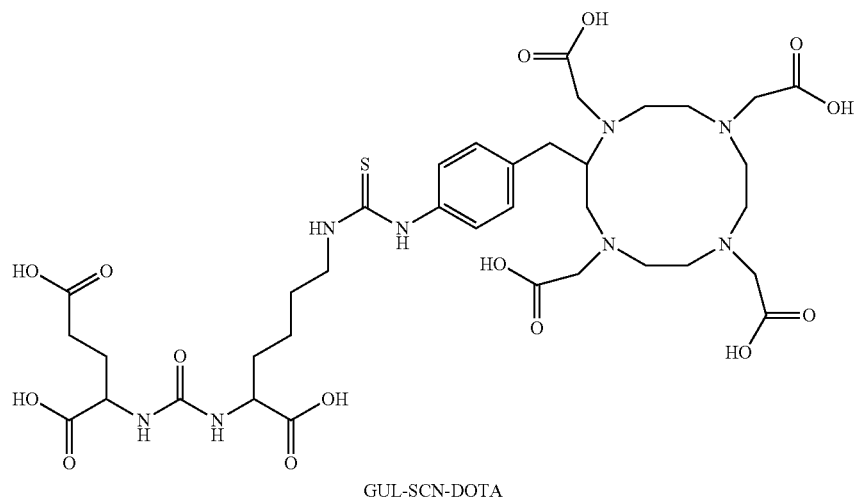

GUL-SCN-DOTA 2,2',2"-(2-(4-(3-((S)-6-(tert-butoxy)-5-(3-((S)-1,5-di-tert-butoxy-1,5-dioxopentane-2-yl)ureido)-6-oxohexyl)thioureido)benzyl)-1,4,7,10-tetraazacyclododecane-1,4,7,10-tetriyl)tetraacetic acid prepared in step 1 was dissolved in 2.0 mL of TFA/DCM (v/v: 1/1) solution, followed by stirring at room temperature for 4 hours. Upon completion of the reaction, the reaction mixture was dried under reduced pressure. The product was washed with DC containing 10% MeOH and as a result GUL-DOTA was obtained as a white powder with the yield of 43%. The molecular weight of the product was calculated by LC/MS.

Mass spectrum (ESI$^+$), m/z=871 [M+H]$^+$ observed.

Example 5: Preparation of Ga-68-DOTA-SCN-GUL

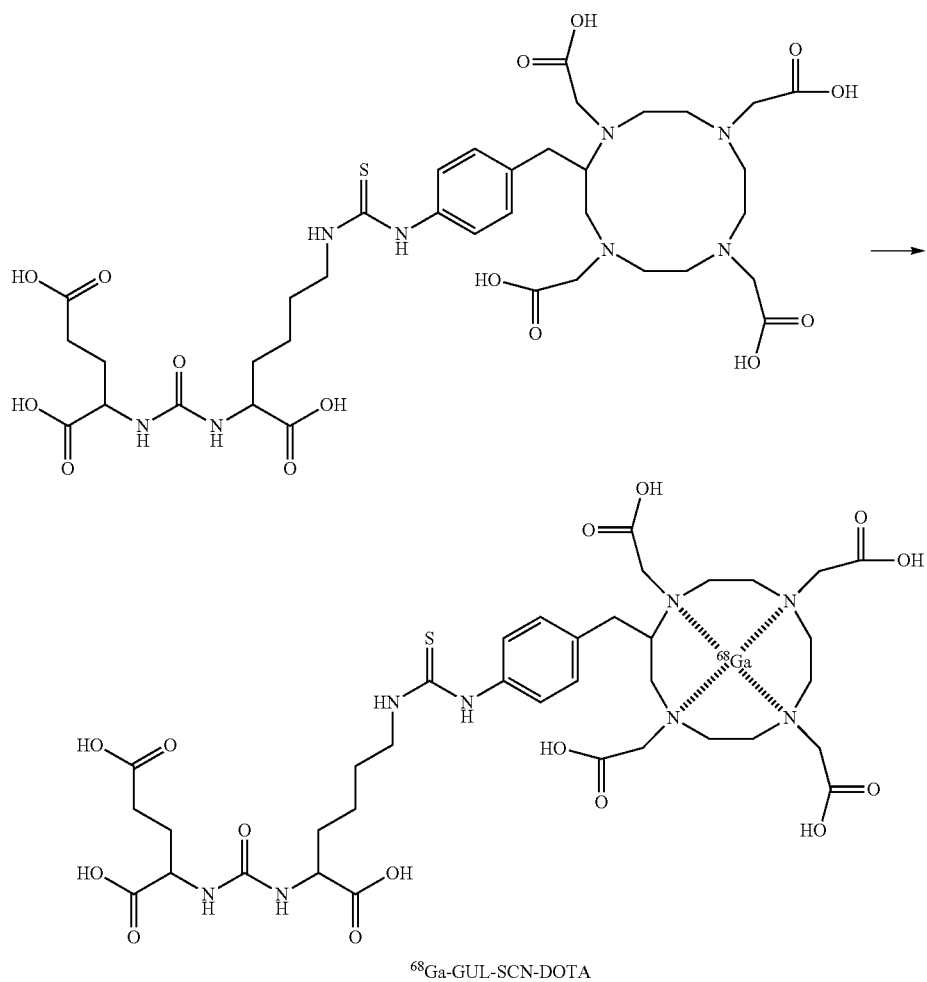

$^{68}$Ga-GUL-SCN-DOTA

MeCN solution containing GUL-DOTA (10 µL, 1 mg/mL) prepared in Example 4 was added thereto, which was vigorously stirred for 1 minute, followed by reaction at 95□ for 10 minutes. The labeling efficiency was calculated by performing ITLC-SG using 0.1 M Na$_2$CO$_3$ as a developing solvent. At this time, the labeled Ga-68-DOTA-SCN-GUL moved to the top (Rf=1.0) (FIG. 2a) and the unlabeled Ga-68 remained at the origin (Rf=0.0) (FIG. 2b). As a result, the labeling efficiency was more than 95%.

Experimental Example 1: Stability Test in Human Serum

The stability in human serum was examined by testing the stability of the compound when it was contacted with human serum. The in vivo stability was tested in vitro.

1. Ga-68-NOTA-SCN-GUL

To investigate the stability of Ga-68-NOTA-SCN-GUL of the present invention in human serum, 3.7 MBq (100 µL) of Ga-68-NOTA-SCN-GUL prepared in Example 3 was added to 1 mL of human serum, which was well mixed, followed by shaking culture at 36.5□. 2 hours later, the reaction mixture was analyzed by ITLC.

As a result, it was confirmed that most of Ga-68-NOTA-SCN-GUL existed as it was without being fallen off to Ga-68 (FIG. 1c).

2. Ga-68-DOTA-SCN-GUL

To investigate the stability of Ga-68-DOTA-SCN-GUL of the present invention in human serum, 3.7 MBq (100 µL) of Ga-68-DOTA-SCN-GUL prepared in Example 5 was added to 1 mL of human serum, which was well mixed, followed by shaking culture at 36.5□. 2 hours later, the reaction mixture was analyzed by ITLC.

As a result, it was confirmed that most of Ga-68-DOTA-SCN-GUL existed as it was, and only 9% of Ga-68-DOTA-SCN-GUL was fallen off to Ga-68 (FIG. 2c).

Therefore, Ga-68-NOTA-SCN-GUL or Ga-68-DOTA-SCN-GUL of the present invention contains thiourea bond which is not hydrolyzed by protease in serum and does not include amide bond, so that it has as excellent stability in human serum as a clear image can be obtained.

Experimental Example 2: In Vitro Competitive Inhibition Cell Binding Test

To perform in vitro competitive inhibition cell binding test of Ga-NOTA-SCN-GUL, the following experiment was conducted.

The PSMA positive prostate cancer cell line 22Rv1 was loaded in a 24-well plate at the density of $2\times10^5$ cells/well, followed by culture in a 37□ 5% $CO_2$ incubator for 24 hours. Ga-NOTA-SCN-GUL prepared in Example 2 was diluted 2-fold serially with the cell culture medium containing 0.5% bovine serum albumin. The diluted sample was added to the cultured cells (0.5 mL/well), to which 1.85 kBq (S)-2-(3-((S)-1-carboxy-5-((4-iodobenzyl)amino)pentyl) ureido)pentanedioic acid (I-125-MIP-1072) was added (0.5 mL/well). After well mixed, the mixture was cultured in a 37□ 5% $CO_2$ incubator for 1 hour. The culture medium was discarded, and the cells were washed with fresh medium twice, to which 0.5% sodium dodecyl sulfate (SDS) dissolved in PBS was added (1 mL/well). The mixture was gently shaken for complete dissolving, and then loaded in a 5 mL disposable plastic test tube. Then, the radioactivity was measured with a gamma counter.

As a result, as the concentration of Ga-NOTA-SCN-GUL of the present invention was increased, the binding between I-125-MIP-1072 and prostate cancer cells was decreased (FIG. 3a). The $IC_{50}$ value was calculated as 18.3 nM by nonlinear regression analysis (FIG. 3b).

Therefore, it was confirmed that Ga-NOTA-SCN-GUL of the present invention was not only excellent in competitive binding to prostate cancer cells but also excellent in suppressing prostate cancer cells at a low concentration.

Experimental Example 3: PET Images of Cancer-Implanted Experimental Animal

Ga-68-NOTA-SCN-GUL of the present invention was administered to the prostate cancer transplanted animal, followed by PET imaging to investigate the cancer tissue targeting as follows.

Particularly, 0.1 mL of RPMI1640 containing $5\times10^6$ cells of 22Rv1 cells was subcutaneously injected into the left lateral side of the male BALB/c nude mouse of 4 weeks old. After 2~3 weeks, the tumor tissue was confirmed to have an appropriate size and used for the experiment. Ga-68-NOTA-SCN-GUL was diluted in injectable saline, resulting in 10.2 MBq/100 µL solution for animal injection. The prepared solution was injected in the tail vein of the cancer cell transplanted mouse. 1 hour later, PET imaging was performed with the animal for 10 minutes.

As a result, Ga-68-NOTA-SCN-GUL of the present invention was excreted in the kidney and absorbed in prostate cancer tissues (FIG. 4a). These kidney excretion images were typically observed in PET images of the isotope-labeled small peptides, indicating that imaging of prostate cancer was possible.

In the case when MIP-1072 that could bind to PSMA was injected before the Ga-68-NOTA-SCN-GUL administration, Ga-68-NOTA-SCN-GUL was not absorbed in prostate cancer tissues (FIG. 4b). This result supported that the prostate cancer images could be obtained by specific binding between Ga-68-NOTA-SCN-GUL and PSMA.

Therefore, it was confirmed that Ga-68-NOTA-SCN-GULGUL of the present invention can specifically bind to PSMA, and accordingly it can be effectively used for imaging prostate cancer.

Experimental Example 4: In Vivo Distribution Test of Cancer-Implanted Experimental Animal Ga-68-NOTA-SCN-GUL or Ga-68-DOTA-SCN-GUL of the present invention was administered to the prostate cancer transplanted animal, followed by in vivo distribution to investigate whether or not the cancer tissue was actually observed therein.

Particularly, 0.1 mL of RPMI1640 containing $5\times10^6$ cells of 22Rv1 cells was subcutaneously injected into the left lateral side of the male BALB/c nude mouse of 4 weeks old. After 2~3 weeks, the tumor tissue was confirmed to have an appropriate size and used for the experiment. Ga-68-NOTA-SCN-GUL prepared in Example 3 or Ga-68-DOTA-SCN-GUL prepared in Example was diluted in injectable saline, resulting in 0.74 MBq/100 µL solution for animal injection. The prepared solution was injected in the tail vein of the cancer cell transplanted mouse. One hour later, tumor, blood, muscle, heart, lung, liver, spleen, stomach, small intestine, kidney, and bone were extracted, and their weights and radioactivity were measured. Based on this data, the intake per unit tissue for dose (% ID/g) was calculated and the results are shown in Table 2.

TABLE 2

| Organ | Example 3 $^{68}$Ga-GUL-SCN-NOTA | Example 5 $^{68}$Ga-GUL-SCN-DOTA |
| --- | --- | --- |
| Blood | 0.17 ± 0.12 | 0.29 ± 0.08 |
| Muscle | 0.04 ± 0.02 | 0.15 ± 0.07 |
| Tumor | 5.40 ± 0.35 | 4.66 ± 0.63 |
| Heart | 0.08 ± 0.04 | 0.26 ± 0.07 |
| Lung | 0.31 ± 0.21 | 0.77 ± 0.17 |
| Liver | 0.19 ± 0.03 | 0.27 ± 0.07 |
| Stomach | 1.38 ± 0.63 | 4.80 ± 0.67 |
| Spleen | 0.10 ± 0.02 | 0.41 ± 0.12 |
| Intestine | 0.20 ± 0.06 | 0.17 ± 0.03 |
| Kidney | 56.12 ± 15.08 | 165.11 ± 8.63 |
| Bone | 0.69 ± 0.20 | 2.20 ± 0.47 |

(In table 2, data represent mean ± standard deviation % ID/g (n = 4).)

As shown in Table 2, Ga-68-NOTA-SCN-GUL or Ga-68-DOTA-SCN-GUL of the present invention was highly absorbed in the kidney, so that the intake in the kidney was as high as or even higher than the conventional radiopharmaceuticals for peptide imaging. The intake was the highest in cancer tissues. The intake of Ga-68-DOTA-SCN-GUL in the spleen was a little higher than that in cancer tissue, which was, though, not statistically significant.

Therefore, it was confirmed that Ga-68-NOTA-SCN-GUL or Ga-68-DOTA-SCN-GUL of the present invention can be effectively used as a radio-active pharmaceutical since it was efficient in prostate cancer imaging.

INDUSTRIAL APPLICABILITY

The present invention relates to a peptide thiourea derivative, a pharmaceutically acceptable salt thereof, a radioisotope labeled compound comprising the same, and a pharmaceutical composition for treating or diagnosing prostate cancer comprising the same as an active ingredient. The peptide thiourea derivative of the present invention is excellent in stability in human serum when it is administered in vivo and not only binds well to PSMA expressed in prostate cancer but also inhibits excellently PSMA at a low concentration. Besides, the derivative of the invention has a high water-solubility and can be excreted into the kidney not into the bile passage so that a clear image of the tumor region of prostate cancer can be obtained. Therefore, the derivative of the present invention can be effectively used as a pharmaceutical composition for treating and diagnosing prostate cancer.

What is claimed is:

1. A compound represented by formula 1 below or a pharmaceutically acceptable salt of the same:

[Formula 1]

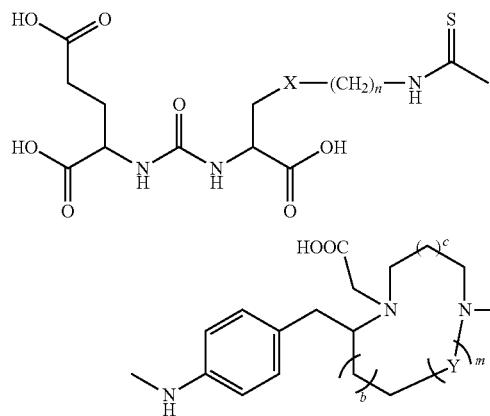

wherein
X is single bond;
n is an integer of 3;
Y is —N(CH$_2$COOH)(CH$_2$)$_a$CH$_2$CH$_2$—,
m is an integer of 1 or 2; and
a, b and c are independently an integer of 0 or 1.

2. The compound or the pharmaceutically acceptable salt of the same according to claim 1, wherein X is single bond; and

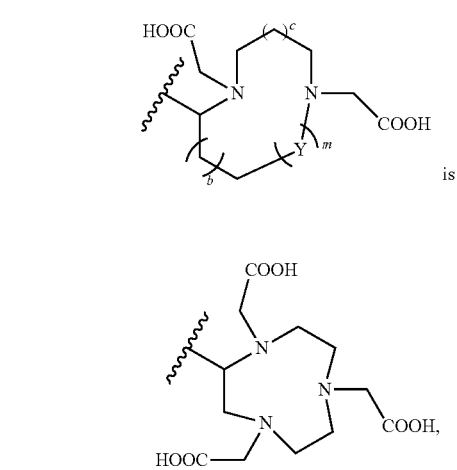

is

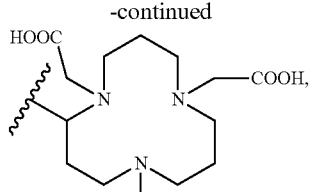

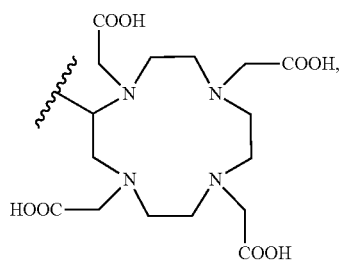

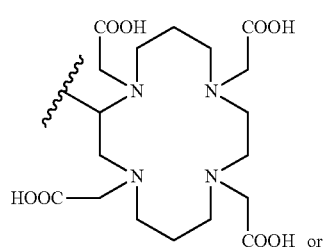

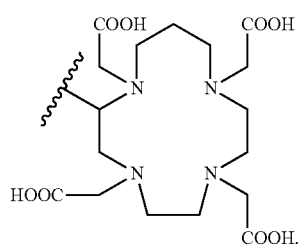

3. A preparation method of the compound represented by formula 1 of claim 1 comprising the step of preparing the compound represented by formula 1 by reacting the compound represented by formula 2 and the compound represented by formula 3 (step 1), as shown in reaction formula 1 below:

[Reaction Formula 1]

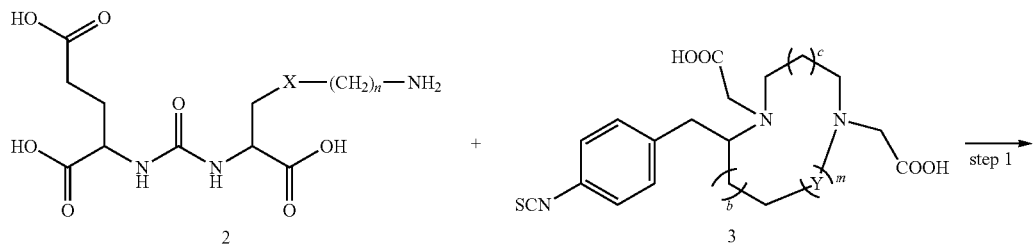

-continued

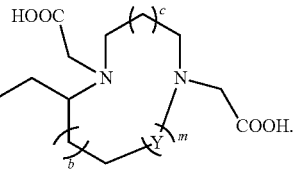
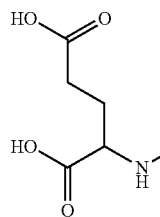

1

4. A labeled compound prepared by coordinating a metallic radio-isotope to the compound represented by formula 1 of claim 1 or the pharmaceutically acceptable salt thereof.

5. The labeled compound according to claim 4, wherein the metallic radio-isotope is $^{67}$Ga, $^{68}$Ga, $^{62}$Cu, $^{64}$Cu, $^{67}$Cu, $^{111}$In, $^{90}$Y, $^{177}$Lu, or $^{117m}$Sn.

6. A pharmaceutical composition for treating or diagnosing prostate cancer comprising the labeled compound of claim 4 as an active ingredient.

7. A radiopharmaceutical for imaging prostate cancer comprising the compound of claim 1 or the pharmaceutically acceptable salt thereof as an active ingredient.

8. A kit for treating or diagnosing prostate cancer comprising the compound of claim 1 or the pharmaceutically acceptable salt thereof.

9. The kit for treating or diagnosing prostate cancer according to claim 8, wherein the kit contains a buffer having the pH of 1 to 9 and the concentration of 1 μM to 10 M.

10. The kit for treating or diagnosing prostate cancer according to claim 9, wherein the buffer is acetic acid, phosphoric acid, citric acid, fumaric acid, ascorbic acid, butyric acid, succinic acid, tartaric acid, carbonic acid, glucoheptonic acid, gluconic acid, glucuronic acid, glucaric acid, boric acid or their sodium salts or potassium salts.

11. A method of treating prostate cancer of a subject comprising administering an effective amount of the compound of claim 1 or the pharmaceutically acceptable salt thereof to the subject.

12. A method of diagnosing prostate cancer of a subject comprising administering an effective amount of the compound of claim 1 or the pharmaceutically acceptable salt thereof to the subject and detecting any absorbed compound indicative of prostate cancer tissue in the subject.

* * * * *